(12) United States Patent
Yonemura et al.

(10) Patent No.: US 9,936,703 B2
(45) Date of Patent: Apr. 10, 2018

(54) CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

(71) Applicant: NIHON NOHYAKU CO., LTD., Tokyo (JP)

(72) Inventors: Ikki Yonemura, Osaka (JP); Kosuke Fukatsu, Osaka (JP); Takashi Furuya, Osaka (JP); Akiyuki Suwa, Osaka (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 220 days.

(21) Appl. No.: 14/771,672

(22) PCT Filed: Mar. 14, 2014

(86) PCT No.: PCT/JP2014/056832
§ 371 (c)(1),
(2) Date: Aug. 31, 2015

(87) PCT Pub. No.: WO2014/142292
PCT Pub. Date: Sep. 18, 2014

(65) Prior Publication Data
US 2016/0021886 A1    Jan. 28, 2016

(30) Foreign Application Priority Data

| Mar. 15, 2013 | (JP) | 2013-053201 |
| May 22, 2013 | (JP) | 2013-107592 |
| Jul. 25, 2013 | (JP) | 2013-155074 |
| Nov. 7, 2013 | (JP) | 2013-231582 |

(51) Int. Cl.
A01N 43/90 (2006.01)
C07D 487/04 (2006.01)

(52) U.S. Cl.
CPC .......... *A01N 43/90* (2013.01); *C07D 487/04* (2013.01)

(58) Field of Classification Search
None
See application file for complete search history.

(56) References Cited

U.S. PATENT DOCUMENTS

| 2011/0039843 A1 | 2/2011 | Iwakoshi et al. |
| 2012/0015975 A1 | 1/2012 | Takahashi et al. |
| 2012/0108586 A1 | 5/2012 | Iwakoshi et al. |
| 2012/0178779 A1 | 7/2012 | Takahashi et al. |
| 2012/0196891 A1 | 8/2012 | Iwakoshi |
| 2012/0245167 A1 | 9/2012 | Iwakoshi et al. |
| 2013/0190271 A1 | 7/2013 | Iwakoshi et al. |
| 2013/0252981 A1 | 9/2013 | Takahashi et al. |

FOREIGN PATENT DOCUMENTS

| JP | 2009-280574 | 12/2009 |
| JP | 2010-275301 | 12/2010 |
| JP | 2011-79774 | 4/2011 |
| JP | 2012-92049 | 5/2012 |
| JP | 2012-92050 | 5/2012 |
| JP | 2012-92051 | 5/2012 |
| JP | 2012-92052 | 5/2012 |

(Continued)

OTHER PUBLICATIONS

Murakami et al., The synthesis of imidazo[4,5-c]- and v-triazolo[4,5-c] pyridazines, 1967, Journal of Heterocyclic Chemistry, vol. 4, Iss.4, abs.*

(Continued)

*Primary Examiner* — Kortney L. Klinkel
*Assistant Examiner* — Tori Strong
(74) *Attorney, Agent, or Firm* — Wenderoth, Lind & Ponack, L.L.P.

(57) ABSTRACT

An object of the present invention is to provide and develop novel agricultural and horticultural insecticides in view of the still immense damage caused by insect pests etc. and the emergence of insect pests resistant to existing insecticides in crop production in the fields of agriculture, horticulture and the like.

Provided are a condensed heterocyclic compound represented by the general formula (I):

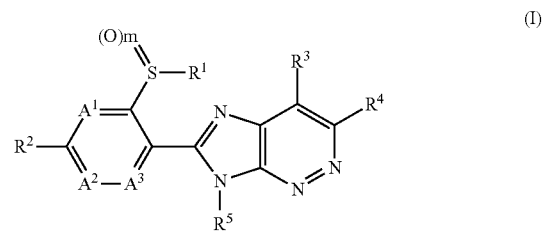

{wherein $A^1$, $A^2$ and $A^3$ may be the same or different, and each represent a nitrogen atom or a CH group, $R^1$ represents an alkyl group or the like, $R^2$ represents a haloalkyl group or the like, $R^3$ represents a hydrogen atom or the like, $R^4$ represents a haloalkyl group or the like, $R^5$ represents an alkyl group or the like, and m represents 0 or 2} or a salt thereof; an agricultural and horticultural insecticide comprising the compound or a salt thereof as an active ingredient; and a method for using the insecticide.

9 Claims, No Drawings

(56) References Cited

FOREIGN PATENT DOCUMENTS

| JP | 2012-92053 | 5/2012 |
|---|---|---|
| JP | 2012-92054 | 5/2012 |
| JP | 2012-92055 | 5/2012 |
| JP | 2012-92056 | 5/2012 |
| JP | 2012-92057 | 5/2012 |
| JP | 2012-92058 | 5/2012 |
| JP | 2012-92059 | 5/2012 |
| JP | 2012-92060 | 5/2012 |
| JP | 2012-92061 | 5/2012 |
| JP | 2012-131780 | 7/2012 |
| WO | 2012/086848 | 6/2012 |
| WO | 2013/018928 | 2/2013 |

OTHER PUBLICATIONS

International Preliminary Report on Patentability dated Sep. 15, 2015 in International (PCT) Application No. PCT/JP2014/056832.
International Search Report dated Apr. 8, 2014 in International (PCT) Application No. PCT/JP2014/056832.

* cited by examiner

CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

TECHNICAL FIELD

The present invention relates to an agricultural and horticultural insecticide comprising a certain kind of condensed heterocyclic compound or a salt thereof as an active ingredient; and the method for using the insecticide.

BACKGROUND ART

Various compounds have been examined for their potential as an agricultural and horticultural insecticide, and among them, certain kinds of condensed heterocyclic compounds have been reported to be useful as an insecticide (for example, see Patent Literature 1 to 6). None of these references disclose any condensed heterocyclic compound containing a pyridazine ring.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2013/018928

SUMMARY OF INVENTION

Technical Problem

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired.

Solution to Problem

The present inventors conducted extensive research to solve the above-described problems. As a result, the present inventors found that a condensed heterocyclic compound represented by the general formula (I) or a salt thereof has an excellent control effect on agricultural and horticultural insect pests, and reached the completion of the present invention.

That is, the present invention relates to the following.

[1] A condensed heterocyclic compound represented by the general formula (I):

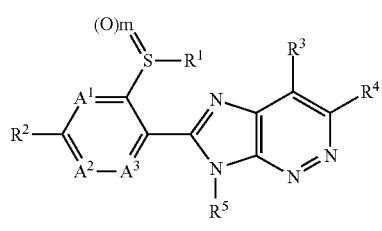

(I)

wherein $R^1$ represents
(a1) a ($C_1$-$C_6$) alkyl group;
(a2) a ($C_3$-$C_6$) cycloalkyl group;
(a3) a ($C_2$-$C_6$) alkenyl group;
(a4) a ($C_2$-$C_6$) alkynyl group;
(a5) a halo ($C_1$-$C_6$) alkyl group;
(a6) a halo ($C_3$-$C_6$) cycloalkyl group;
(a7) a halo ($C_2$-$C_6$) alkenyl group;
(a8) a halo ($C_2$-$C_6$) alkynyl group;
(a9) a ($C_1$-$C_6$) alkoxy ($C_1$-$C_6$) alkyl group;
(a10) a halo ($C_1$-$C_6$) alkoxy ($C_1$-$C_6$) alkyl group;
(a11) a ($C_3$-$C_6$) cycloalkyl ($C_1$-$C_6$) alkyl group;
(a12) a halo ($C_3$-$C_6$) cycloalkyl ($C_1$-$C_6$) alkyl group;
(a13) a ($C_1$-$C_6$) alkoxy halo ($C_1$-$C_6$) alkyl group;
(a14) a halo ($C_1$-$C_6$) alkoxy halo ($C_1$-$C_6$) alkyl group;
(a15) a ($C_1$-$C_6$) alkylthio ($C_1$-$C_6$) alkyl group;
(a16) a ($C_1$-$C_6$) alkylsulfinyl ($C_1$-$C_6$) alkyl group;
(a17) a ($C_1$-$C_6$) alkylsulfonyl ($C_1$-$C_6$) alkyl group;
(a18) a cyano ($C_1$-$C_6$) alkyl group;
(a19) a ($C_1$-$C_6$) alkoxycarbonyloxy ($C_1$-$C_6$) alkyl group;
(a20) a di-($C_1$-$C_6$) alkylamino ($C_1$-$C_6$) alkyl group (wherein the alkyl groups of the di-($C_1$-$C_6$) alkylamino moiety may be the same or different);
(a21) a phenyl ($C_1$-$C_6$) alkyl group; or
(a22) a phenyl ($C_1$-$C_6$) alkyl group having, on the ring, 1 to 5 substituting groups selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group,
$R^2$ represents
(b1) a halogen atom;
(b2) a cyano group;
(b3) a nitro group;
(b4) a ($C_1$-$C_6$) alkyl group;
(b5) ($C_3$-$C_6$) cycloalkyl group;
(b6) a ($C_2$-$C_6$) alkenyl group;
(b7) a ($C_2$-$C_6$) alkynyl group;
(b8) a halo ($C_1$-$C_6$) alkyl group;
(b9) a halo ($C_3$-$C_6$) cycloalkyl group;
(b10) a halo ($C_2$-$C_6$) alkenyl group;
(b11) a halo ($C_2$-$C_6$) alkynyl group;
(b12) a ($C_1$-$C_6$) alkylthio group;
(b13) a ($C_1$-$C_6$) alkylsulfinyl group;
(b14) a ($C_1$-$C_6$) alkylsulfonyl group;
(b15) a halo ($C_1$-$C_6$) alkylthio group;
(b16) a halo ($C_1$-$C_6$) alkylsulfinyl group;
(b17) a halo ($C_1$-$C_6$) alkylsulfonyl group;
(b18) a ($C_1$-$C_6$) alkoxy ($C_1$-$C_6$) alkyl group;
(b19) a halo ($C_1$-$C_6$) alkoxy ($C_1$-$C_6$) alkyl group;
(b20) a ($C_3$-$C_6$) cycloalkyl ($C_1$-$C_6$) alkyl group;
(b21) a halo ($C_3$-$C_6$) cycloalkyl ($C_1$-$C_6$) alkyl group;
(b22) a ($C_1$-$C_6$) alkoxy halo ($C_1$-$C_6$) alkyl group;
(b23) a halo ($C_1$-$C_6$) alkoxy halo ($C_1$-$C_6$) alkyl group;
(b24) a hydrogen atom;
(b25) a ($C_1$-$C_6$) alkoxy group;
(b26) a halo ($C_1$-$C_6$) alkoxy group;
(b27) an amino group;
(b28) a ($C_1$-$C_6$) alkylamino group;
(b29) a di-($C_1$-$C_6$) alkylamino group (wherein the alkyl groups of the di-($C_1$-$C_6$) alkyl moiety may be the same or different);
(b30) a ($C_1$-$C_6$) alkylcarbonylamino group;
(b31) a ($C_1$-$C_6$) alkylsulfonylamino group;
(b32) a ($C_1$-$C_6$) alkylsulfonyl (($C_1$-$C_6$) alkyl) amino group;
(b33) a ($C_1$-$C_6$) alkoxycarbonyl group; or (b34) a tri-($C_1$-$C_6$) alkylsilyl ($C_2$-$C_6$) alkynyl group (wherein the alkyl groups of the tri-($C_1$-$C_6$) alkylsilyl moiety may be the same or different), $R^3$ represents
(c1) a hydrogen atom;
(c2) a halogen atom;
(c3) a cyano group;
(c4) a nitro group;
(c5) a ($C_1$-$C_6$) alkyl group;
(c6) a ($C_1$-$C_6$) alkoxy group;
(c7) a ($C_2$-$C_6$) alkenyloxy group;
(c8) a ($C_2$-$C_6$) alkynyloxy group;
(c9) a halo ($C_1$-$C_6$) alkyl group;
(c10) a halo ($C_1$-$C_6$) alkoxy group;
(c11) a halo ($C_2$-$C_6$) alkenyloxy group;
(c12) a halo ($C_2$-$C_6$) alkynyloxy group;
(c13) a ($C_1$-$C_6$) alkoxy ($C_1$-$C_6$) alkyl group;
(c14) a halo ($C_1$-$C_6$) alkoxy ($C_1$-$C_6$) alkyl group;
(c15) a ($C_3$-$C_6$) cycloalkyl ($C_1$-$C_6$) alkyl group;
(c16) a halo ($C_3$-$C_6$) cycloalkyl ($C_1$-$C_6$) alkyl group;
(c17) a ($C_1$-$C_6$) alkoxy halo ($C_1$-$C_6$) alkyl group; or
(c18) a halo ($C_1$-$C_6$) alkoxy halo ($C_1$-$C_6$) alkyl group, $R^4$ represents
(d1) a hydrogen atom;
(d2) a halogen atom;
(d3) a cyano group;
(d4) a nitro group;
(d5) a ($C_1$-$C_6$) alkyl group;
(d6) a ($C_1$-$C_6$) alkoxy group;
(d7) a ($C_2$-$C_6$) alkenyloxy group;
(d8) a ($C_2$-$C_6$) alkynyloxy group;
(d9) a halo ($C_1$-$C_6$) alkyl group;
(d10) a halo ($C_1$-$C_6$) alkoxy group;
(d11) a halo ($C_2$-$C_6$) alkenyloxy group;
(d12) a halo ($C_2$-$C_6$) alkynyloxy group;
(d13) a ($C_1$-$C_6$) alkoxy ($C_1$-$C_6$) alkyl group;
(d14) a halo ($C_1$-$C_6$) alkoxy ($C_1$-$C_6$) alkyl group;
(d15) a ($C_3$-$C_6$) cycloalkyl ($C_1$-$C_6$) alkyl group;
(d16) a halo ($C_3$-$C_6$) cycloalkyl ($C_1$-$C_6$) alkyl group;
(d17) a ($C_1$-$C_6$) alkoxy halo ($C_1$-$C_6$) alkyl group;
(d18) a halo ($C_1$-$C_6$) alkoxy halo ($C_1$-$C_6$) alkyl group;
(d19) a mercapto group;
(d20) a ($C_1$-$C_6$) alkylthio group;
(d21) a ($C_1$-$C_6$) alkylcarbonylthio group;
(d22) a halo ($C_1$-$C_6$) alkylthio group;
(d23) a phenyl group;
(d24) a phenyl group having, on the ring, 1 to 5 substituting groups selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
(d25) a ($C_1$-$C_6$) alkylsulfinyl group;
(d26) a ($C_1$-$C_6$) alkylsulfonyl group;
(d27) a halo ($C_1$-$C_6$) alkylsulfinyl group; or
(d28) a halo ($C_1$-$C_6$) alkylsulfonyl group, $R^5$ represents
(e1) a hydrogen atom;
(e2) a formyl group;
(e3) a ($C_1$-$C_6$) alkyl group;
(e4) a ($C_3$-$C_6$) cycloalkyl group;
(e5) a halo ($C_1$-$C_6$) alkyl group;
(e6) a halo ($C_3$-$C_6$) cycloalkyl group;
(e7) a ($C_1$-$C_6$) alkylsulfonyl group;
(e8) a halo ($C_1$-$C_6$) alkylsulfonyl group;
(e9) a ($C_1$-$C_6$) alkoxy ($C_1$-$C_6$) alkyl group;
(e10) a halo ($C_1$-$C_6$) alkoxy ($C_1$-$C_6$) alkyl group;
(e11) a ($C_1$-$C_6$) alkoxy halo ($C_1$-$C_6$) alkyl group;
(e12) a halo ($C_1$-$C_6$) alkoxy halo ($C_1$-$C_6$) alkyl group;
(e13) an amino group; or
(e14) a ($C_1$-$C_6$) alkoxy group, $A^1$, $A^2$ and $A^3$ may be the same or different, and each represent a nitrogen atom or a C—$R^6$ group (wherein $R^6$ represents
(f1) a hydrogen atom;
(f2) a halogen atom;
(f3) a cyano group;
(f4) a nitro group;
(f5) a formyl group;
(f6) a ($C_1$-$C_6$) alkyl group;
(f7) a ($C_1$-$C_6$) alkoxy group;
(f8) a ($C_2$-$C_6$) alkenyloxy group;
(f9) a ($C_2$-$C_6$) alkynyloxy group;
(f10) a ($C_3$-$C_6$) cycloalkoxy group;
(f11) a halo ($C_1$-$C_6$) alkyl group;
(f12) a halo ($C_1$-$C_6$) alkoxy group;
(f13) a halo ($C_2$-$C_6$) alkenyloxy group;
(f14) a halo ($C_2$-$C_6$) alkynyloxy group;
(f15) a halo ($C_3$-$C_6$) cycloalkoxy group;
(f16) a ($C_1$-$C_6$) alkylthio group;
(f17) a ($C_1$-$C_6$) alkylsulfinyl group;
(f18) a ($C_1$-$C_6$) alkylsulfonyl group;
(f19) a halo ($C_1$-$C_6$) alkylthio group;
(f20) a halo ($C_1$-$C_6$) alkylsulfinyl group;
(f21) a halo ($C_1$-$C_6$) alkylsulfonyl group;
(f22) a ($C_1$-$C_6$) alkoxy ($C_1$-$C_6$) alkyl group;
(f23) a halo ($C_1$-$C_6$) alkoxy ($C_1$-$C_6$) alkyl group;
(f24) a ($C_1$-$C_6$) alkoxy halo ($C_1$-$C_6$) alkyl group; or
(f25) a halo ($C_1$-$C_6$) alkoxy halo ($C_1$-$C_6$) alkyl group), and
m represents 0, 1 or 2, and
a salt thereof.

[2] The condensed heterocyclic compound according to the above [1],
wherein $R^1$ is
(a1) a ($C_1$-$C_6$) alkyl group;
(a2) a ($C_3$-$C_6$) cycloalkyl group;
(a3) a ($C_2$-$C_6$) alkenyl group;
(a4) a ($C_2$-$C_6$) alkynyl group;
(a5) a halo ($C_1$-$C_6$) alkyl group;
(a9) a ($C_1$-$C_6$) alkoxy ($C_1$-$C_6$) alkyl group;
(a11) a ($C_3$-$C_6$) cycloalkyl ($C_1$-$C_6$) alkyl group;
(a15) a ($C_1$-$C_6$) alkylthio ($C_1$-$C_6$) alkyl group;
(a16) a ($C_1$-$C_6$) alkylsulfinyl ($C_1$-$C_6$) alkyl group;
(a17) a ($C_1$-$C_6$) alkylsulfonyl ($C_1$-$C_6$) alkyl group;
(a18) a cyano ($C_1$-$C_6$) alkyl group;
(a19) a ($C_1$-$C_6$) alkoxycarbonyloxy ($C_1$-$C_6$) alkyl group;
(a20) a di-($C_1$-$C_6$) alkylamino ($C_1$-$C_6$) alkyl group (wherein the alkyl groups of the dialkylamino moiety may be the same or different);
(a21) a phenyl ($C_1$-$C_6$) alkyl group; or
(a22) a phenyl ($C_1$-$C_6$) alkyl group having, on the ring, 1 to 5 substituting groups selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group, $R^2$ is
(b1) a halogen atom;
(b4) a ($C_1$-$C_6$) alkyl group;
(b5) a ($C_3$-$C_6$) cycloalkyl group;
(b6) a ($C_2$-$C_6$) alkenyl group;
(b7) a ($C_2$-$C_6$) alkynyl group;
(b8) a halo ($C_1$-$C_6$) alkyl group;
(b12) a ($C_1$-$C_6$) alkylthio group;
(b15) a halo ($C_1$-$C_6$) alkylthio group;

(b16) a halo $(C_1$-$C_6)$ alkylsulfinyl group;
(b17) a halo $(C_1$-$C_6)$ alkylsulfonyl group;
(b24) a hydrogen atom;
(b25) a $(C_1$-$C_6)$ alkoxy group;
(b26) a halo $(C_1$-$C_6)$ alkoxy group;
(b27) an amino group;
(b29) a di-$(C_1$-$C_6)$ alkylamino group (wherein the alkyl groups of the di-$(C_1$-$C_6)$ alkyl moiety may be the same or different);
(b30) a $(C_1$-$C_6)$ alkylcarbonylamino group;
(b31) a $(C_1$-$C_6)$ alkylsulfonylamino group;
(b32) a $(C_1$-$C_6)$ alkylsulfonyl $((C_1$-$C_6)$ alkyl) amino group;
(b33) a $(C_1$-$C_6)$ alkoxycarbonyl group; or
(b34) a tri-$(C_1$-$C_6)$ alkylsilyl $(C_2$-$C_6)$ alkynyl group (wherein the alkyl groups of the tri-$(C_1$-$C_6)$ alkylsilyl moiety may be the same or different),
$R^3$ is (c1) a hydrogen atom,
$R^4$ is
(d2) a halogen atom;
(d5) a $(C_1$-$C_6)$ alkyl group;
(d9) a halo $(C_1$-$C_6)$ alkyl group;
(d19) a mercapto group;
(d20) a $(C_1$-$C_6)$ alkylthio group;
(d21) a $(C_1$-$C_6)$ alkylcarbonylthio group;
(d22) a halo $(C_1$-$C_6)$ alkylthio group;
(d24) a phenyl group having, on the ring, 1 to 5 substituting groups selected from the group consisting of (a) a halogen atom, (b) a cyano group, (c) a nitro group, (d) a $(C_1$-$C_6)$ alkyl group, (e) a $(C_1$-$C_6)$ alkoxy group, (f) a halo $(C_1$-$C_6)$ alkyl group and (g) a halo $(C_1$-$C_6)$ alkoxy group; or
(d26) a $(C_1$-$C_6)$ alkylsulfonyl group,
$R^5$ is
(e3) a $(C_1$-$C_6)$ alkyl group;
(e4) a $(C_3$-$C_6)$ cycloalkyl group;
(e5) a halo $(C_1$-$C_6)$ alkyl group;
(e9) a $(C_1$-$C_6)$ alkoxy $(C_1$-$C_6)$ alkyl group;
(e13) an amino group; or
(e14) a $(C_1$-$C_6)$ alkoxy group, and
$A^1$, $A^2$ and $A^3$ may be the same or different, and each represent a nitrogen atom or a C—$R^6$ group (wherein $R^6$ is (f1) a hydrogen atom), and
a salt thereof.
[3] The condensed heterocyclic compound according to the above [1],
wherein $R^1$ is
(a1) a $(C_1$-$C_6)$ alkyl group;
(a2) a $(C_3$-$C_6)$ cycloalkyl group;
(a3) a $(C_2$-$C_6)$ alkenyl group;
(a5) a halo $(C_1$-$C_6)$ alkyl group;
(a11) a $(C_3$-$C_6)$ cycloalkyl $(C_1$-$C_6)$ alkyl group;
(a15) a $(C_1$-$C_6)$ alkylthio $(C_1$-$C_6)$ alkyl group;
(a18) a cyano $(C_1$-$C_6)$ alkyl group;
(a19) a $(C_1$-$C_6)$ alkoxycarbonyloxy $(C_1$-$C_6)$ alkyl group;
(a20) a di-$(C_1$-$C_6)$ alkylamino $(C_1$-$C_6)$ alkyl group (wherein the alkyl groups of the di-$(C_1$-$C_6)$ alkylamino moiety may be the same or different); or
(a22) a phenyl $(C_1$-$C_6)$ alkyl group having, on the ring, 1 to 5 substituting groups selected from the group consisting of (a) a halogen atom, (b) a cyano group, (c) a nitro group, (d) a $(C_1$-$C_6)$ alkyl group, (e) a $(C_1$-$C_6)$ alkoxy group, (f) a halo $(C_1$-$C_6)$ alkyl group and (g) a halo $(C_1$-$C_6)$ alkoxy group,
$R^2$ is
(b1) a halogen atom;
(b4) a $(C_1$-$C_6)$ alkyl group;
(b5) a $(C_3$-$C_6)$ cycloalkyl group;
(b6) a $(C_2$-$C_6)$ alkenyl group;
(b7) a $(C_2$-$C_6)$ alkynyl group;
(b8) a halo $(C_1$-$C_6)$ alkyl group;
(b12) a $(C_1$-$C_6)$ alkylthio group;
(b15) a halo $(C_1$-$C_6)$ alkylthio group;
(b24) a hydrogen atom;
(b26) a halo $(C_1$-$C_6)$ alkoxy group;
(b27) an amino group;
(b29) a di-$(C_1$-$C_6)$ alkylamino group (wherein the alkyl groups of the di-$(C_1$-$C_6)$ alkyl moiety may be the same or different);
(b30) a $(C_1$-$C_6)$ alkylcarbonylamino group;
(b31) a $(C_1$-$C_6)$ alkylsulfonylamino group;
(b32) a $(C_1$-$C_6)$ alkylsulfonyl $((C_1$-$C_6)$ alkylamino group;
(b33) a $(C_1$-$C_6)$ alkoxycarbonyl group; or
(b34) a tri-$(C_1$-$C_6)$ alkylsilyl $(C_2$-$C_6)$ alkynyl group (wherein the alkyl groups of the tri-$(C_1$-$C_6)$ alkylsilyl moiety may be the same or different),
$R^3$ is (c1) a hydrogen atom,
$R^4$ is
(d2) a halogen atom;
(d9) a halo $(C_1$-$C_6)$ alkyl group;
(d19) a mercapto group;
(d20) a $(C_1$-$C_6)$ alkylthio group;
(d21) a $(C_1$-$C_6)$ alkylcarbonylthio group;
(d22) a halo $(C_1$-$C_6)$ alkylthio group;
(d24) a phenyl group having, on the ring, 1 to 5 substituting groups selected from the group consisting of (a) a halogen atom, (b) a cyano group, (c) a nitro group, (d) a $(C_1$-$C_6)$ alkyl group, (e) a $(C_1$-$C_6)$ alkoxy group, (f) a halo $(C_1$-$C_6)$ alkyl group and (g) a halo $(C_1$-$C_6)$ alkoxy group; or
(d26) a $(C_1$-$C_6)$ alkylsulfonyl group,
$R^5$ is
(e3) a $(C_1$-$C_6)$ alkyl group;
(e4) a $(C_3$-$C_6)$ cycloalkyl group; or
(e9) a $(C_1$-$C_6)$ alkoxy $(C_1$-$C_6)$ alkyl group, and
$A^1$, $A^2$ and $A^3$ may be the same or different, and each represent a nitrogen atom or a C—$R^6$ group (wherein $R^6$ is (f1) a hydrogen atom), and
a salt thereof.
[4] Use of the condensed heterocyclic compound or a salt thereof according to any one of the above [1] to [3] as an agricultural and horticultural insecticide.
[5] A method for using an agricultural and horticultural insecticide, comprising treating plants or soil with an active ingredient of the agricultural and horticultural insecticide according to the above [4].
[6] A method for controlling agricultural and horticultural insect pests, comprising treating plants or soil with an effective amount of the agricultural and horticultural insecticide according to the above [4].
[7] An ectoparasite control agent comprising the condensed heterocyclic compound or a salt thereof according to any one of the above [1] to [3] as an active ingredient.
[8] A method for controlling ectoparasites, comprising treating ectoparasites with an effective amount of the ectoparasite control agent according to the above [7].
[9] An insecticide comprising an imidazopyridazine-containing condensed heterocyclic compound exemplified by the general formula (I) or a salt thereof as an active ingredient.
[10] The insecticide according to the above [9], wherein the imidazopyridazine-containing condensed heterocyclic compound is a condensed heterocyclic compound containing imidazo[4,5-C]pyridazine.
The present invention also relates to the following.
[11] A condensed heterocyclic compound represented by the general formula (I):

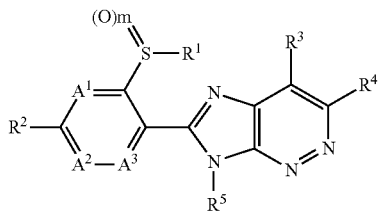

wherein R¹ represents
(a1) a $(C_1-C_6)$ alkyl group;
(a2) a $(C_3-C_6)$ cycloalkyl group;
(a3) a $(C_2-C_6)$ alkenyl group;
(a4) a $(C_2-C_6)$ alkynyl group;
(a5) a halo $(C_1-C_6)$ alkyl group;
(a6) a halo $(C_3-C_6)$ cycloalkyl group;
(a7) a halo $(C_2-C_6)$ alkenyl group;
(a8) a halo $(C_2-C_6)$ alkynyl group;
(a9) a $(C_1-C_6)$ alkoxy $(C_1-C_6)$ alkyl group;
(a10) a halo $(C_1-C_6)$ alkoxy $(C_1-C_6)$ alkyl group;
(a11) a $(C_3-C_6)$ cycloalkyl $(C_1-C_6)$ alkyl group;
(a12) a halo $(C_3-C_6)$ cycloalkyl $(C_1-C_6)$ alkyl group;
(a13) a $(C_1-C_6)$ alkoxy halo $(C_1-C_6)$ alkyl group; or
(a14) a halo $(C_1-C_6)$ alkoxy halo $(C_1-C_6)$ alkyl group,
R² represents
(b1) a halogen atom;
(b2) a cyano group;
(b3) a nitro group;
(b4) a $(C_1-C_6)$ alkyl group;
(b5) a $(C_3-C_6)$ cycloalkyl group;
(b6) a $(C_2-C_6)$ alkenyl group;
(b7) a $(C_2-C_6)$ alkynyl group;
(b8) a halo $(C_1-C_6)$ alkyl group;
(b9) a halo $(C_3-C_6)$ cycloalkyl group;
(b10) a halo $(C_2-C_6)$ alkenyl group;
(b11) a halo $(C_2-C_6)$ alkynyl group;
(b12) a $(C_1-C_6)$ alkylthio group;
(b13) a $(C_1-C_6)$ alkylsulfinyl group;
(b14) a $(C_1-C_6)$ alkylsulfonyl group;
(b15) a halo $(C_1-C_6)$ alkylthio group;
(b16) a halo $(C_1-C_6)$ alkylsulfinyl group;
(b17) a halo $(C_1-C_6)$ alkylsulfonyl group;
(b18) a $(C_1-C_6)$ alkoxy $(C_1-C_6)$ alkyl group;
(b19) a halo $(C_1-C_6)$ alkoxy $(C_1-C_6)$ alkyl group;
(b20) a $(C_3-C_6)$ cycloalkyl $(C_1-C_6)$ alkyl group;
(b21) a halo $(C_3-C_6)$ cycloalkyl $(C_1-C_6)$ alkyl group;
(b22) a $(C_1-C_6)$ alkoxy halo $(C_1-C_6)$ alkyl group; or
(b23) a halo $(C_1-C_6)$ alkoxy halo $(C_1-C_6)$ alkyl group,
R³ represents
(c1) a hydrogen atom;
(c2) a halogen atom;
(c3) a cyano group;
(c4) a nitro group;
(c5) a $(C_1-C_6)$ alkyl group;
(c6) a $(C_1-C_6)$ alkoxy group;
(c7) a $(C_2-C_6)$ alkenyloxy group;
(c8) a $(C_2-C_6)$ alkynyloxy group;
(c9) a halo $(C_1-C_6)$ alkyl group;
(c10) a halo $(C_1-C_6)$ alkoxy group;
(c11) a halo $(C_2-C_6)$ alkenyloxy group;
(c12) a halo $(C_2-C_6)$ alkynyloxy group;
(c13) a $(C_1-C_6)$ alkoxy $(C_1-C_6)$ alkyl group;
(c14) a halo $(C_1-C_6)$ alkoxy $(C_1-C_6)$ alkyl group;
(c15) a $(C_3-C_6)$ cycloalkyl $(C_1-C_6)$ alkyl group;
(c16) a halo $(C_3-C_6)$ cycloalkyl $(C_1-C_6)$ alkyl group;
(c17) a $(C_1-C_6)$ alkoxy halo $(C_1-C_6)$ alkyl group; or
(c18) a halo $(C_1-C_6)$ alkoxy halo $(C_1-C_6)$ alkyl group,
R⁴ represents
(d1) a hydrogen atom;
(d2) a halogen atom;
(d3) a cyano group;
(d4) a nitro group;
(d5) a $(C_1-C_6)$ alkyl group;
(d6) a $(C_1-C_6)$ alkoxy group;
(d7) a $(C_2-C_6)$ alkenyloxy group;
(d8) a $(C_2-C_6)$ alkynyloxy group;
(d9) a halo $(C_1-C_6)$ alkyl group;
(d10) a halo $(C_1-C_6)$ alkoxy group;
(d11) a halo $(C_2-C_6)$ alkenyloxy group;
(d12) a halo $(C_2-C_6)$ alkynyloxy group;
(d13) a $(C_1-C_6)$ alkoxy $(C_1-C_6)$ alkyl group;
(d14) a halo $(C_1-C_6)$ alkoxy $(C_1-C_6)$ alkyl group;
(d15) a $(C_3-C_6)$ cycloalkyl $(C_1-C_6)$ alkyl group;
(d16) a halo $(C_3-C_6)$ cycloalkyl $(C_1-C_6)$ alkyl group;
(d17) a $(C_1-C_6)$ alkoxy halo $(C_1-C_6)$ alkyl group; or
(d18) a halo $(C_1-C_6)$ alkoxy halo $(C_1-C_6)$ alkyl group,
R⁵ represents
(e1) a hydrogen atom;
(e2) a formyl group;
(e3) a $(C_1-C_6)$ alkyl group;
(e4) a $(C_3-C_6)$ cycloalkyl group;
(e5) a halo $(C_1-C_6)$ alkyl group;
(e6) a halo $(C_3-C_6)$ cycloalkyl group;
(e7) a $(C_1-C_6)$ alkylsulfonyl group;
(e8) a halo $(C_1-C_6)$ alkylsulfonyl group;
(e9) a $(C_1-C_6)$ alkoxy $(C_1-C_6)$ alkyl group;
(e10) a halo $(C_1-C_6)$ alkoxy $(C_1-C_6)$ alkyl group;
(e11) a $(C_1-C_6)$ alkoxy halo $(C_1-C_6)$ alkyl group; or
(e12) a halo $(C_1-C_6)$ alkoxy halo $(C_1-C_6)$ alkyl group,
A¹, A² and A³ may be the same or different, and each represent a nitrogen atom or a C—R⁶ group (wherein R⁶ represents
(f1) a hydrogen atom;
(f2) a halogen atom;
(f3) a cyano group;
(f4) a nitro group;
(f5) a formyl group;
(f6) a $(C_1-C_6)$ alkyl group;
(f7) a $(C_1-C_6)$ alkoxy group;
(f8) a $(C_2-C_6)$ alkenyloxy group;
(f9) a $(C_2-C_6)$ alkynyloxy group;
(f10) a $(C_3-C_6)$ cycloalkoxy group;
(f11) a halo $(C_1-C_6)$ alkyl group;
(f12) a halo $(C_1-C_6)$ alkoxy group;
(f13) a halo $(C_2-C_6)$ alkenyloxy group;
(f14) a halo $(C_2-C_6)$ alkynyloxy group;
(f15) a halo $(C_3-C_6)$ cycloalkoxy group;
(f16) a $(C_1-C_6)$ alkylthio group;
(f17) a $(C_1-C_6)$ alkylsulfinyl group;
(f18) a $(C_1-C_6)$ alkylsulfonyl group;
(f19) a halo $(C_1-C_6)$ alkylthio group;
(f20) a halo $(C_1-C_6)$ alkylsulfinyl group;
(f21) a halo $(C_1-C_6)$ alkylsulfonyl group;
(f22) a $(C_1-C_6)$ alkoxy $(C_1-C_6)$ alkyl group;
(f23) a halo $(C_1-C_6)$ alkoxy $(C_1-C_6)$ alkyl group;
(f24) a $(C_1-C_6)$ alkoxy halo $(C_1-C_6)$ alkyl group; or
(f25) a halo $(C_1-C_6)$ alkoxy halo $(C_1-C_6)$ alkyl group), and
m represents 0, 1 or 21, and
a salt thereof.

[12] The condensed heterocyclic compound according to the above [11],
wherein $R^1$ is (a1) a ($C_1$-$C_6$) alkyl group,
$R^2$ is
(b1) a halogen atom;
(b4) a ($C_1$-$C_6$) alkyl group; or
(b8) a halo ($C_1$-$C_6$) alkyl group,
$R^3$ is (c1) a hydrogen atom,
$R^4$ is (d9) a halo ($C_1$-$C_6$) alkyl group,
$R^5$ is
(e3) a ($C_1$-$C_6$) alkyl group; or
(e4) a ($C_3$-$C_6$) cycloalkyl group,
$A^1$, $A^2$ and $A^3$ are each a C—$R^6$ group (wherein $R^6$ is (f1) a hydrogen atom), and
m is 0 or 2, and
a salt thereof.
[13] The condensed heterocyclic compound according to the above [11],
wherein $R^1$ is (a1) a ($C_1$-$C_6$) alkyl group,
$R^2$ is (b8) a halo ($C_1$-$C_6$) alkyl group,
$R^3$ is (c1) a hydrogen atom,
$R^4$ is (d9) a halo ($C_1$-$C_6$) alkyl group,
$R^5$ is (e3) a ($C_1$-$C_6$) alkyl group,
$A^1$, $A^2$ and $A^3$ are each a C—$R^6$ group (wherein $R^6$ is (f1) a hydrogen atom), and
m is 0 or 2, and
a salt thereof.
[14] Use of the condensed heterocyclic compound or a salt thereof according to any one of the above [11] to [13] as an agricultural and horticultural insecticide.
[15] A method for using an agricultural and horticultural insecticide, comprising treating plants or soil with an active ingredient of the agricultural and horticultural insecticide according to the above [14].
[16] A method for controlling agricultural and horticultural insect pests, comprising treating plants or soil with an effective amount of the agricultural and horticultural insecticide according to the above [14].
[17] An ectoparasite control agent comprising the condensed heterocyclic compound or a salt thereof according to any one of the above [11] to [13] as an active ingredient.
[18] A method for controlling ectoparasites, comprising treating ectoparasites with an effective amount of the ectoparasite control agent according to the above [17].
[19] An insecticide comprising an imidazopyridazine-containing condensed heterocyclic compound exemplified by the general formula (I) or a salt thereof as an active ingredient.
[20] The insecticide according to the above [19], wherein the imidazopyridazine-containing condensed heterocyclic compound is a condensed heterocyclic compound containing imidazo[4,5-C]pyridazine Advantageous Effects of Invention The condensed heterocyclic compound of the present invention or a salt thereof is not only highly effective as an agricultural and horticultural insecticide, but also is effective against pests which live on the exterior of or in the interior of pets such as dogs and cats and domestic animals such as cattle and sheep.

DESCRIPTION OF EMBODIMENTS

In the definition of the general formula (I) representing the condensed heterocyclic compound of the present invention or a salt thereof, "halo" refers to a "halogen atom" and represents a chlorine atom, a bromine atom, an iodine atom or a fluorine atom.

The "($C_1$-$C_6$) alkyl group" refers to a straight chain or branched chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like. The "($C_2$-$C_6$) alkenyl group" refers to a straight chain or branched chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group or the like. The "($C_2$-$C_6$) alkynyl group" refers to a straight chain or branched chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a1-hexynyl group, a 3-methyl-1-butynyl group, a 3,3-dimethyl-1-butynyl group or the like.

The "($C_3$-$C_6$) cycloalkyl group" refers to a cyclic alkyl group of 3 to 6 carbon atoms, for example, a cyclopropyl group, a cyclobutyl group, a cyclopentyl group, a cyclohexyl group or the like. The "($C_1$-$C_6$) alkoxy group" refers to a straight chain or branched chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, a 1-ethylpropyloxy group, a 1-methylbutyloxy group, a n-hexyloxy group, an isohexyloxy group, a 1,1,2-trimethylpropyloxy group or the like. The "($C_2$-$C_6$) alkenyloxy group" refers to a straight chain or branched chain alkenyloxy group of 2 to 6 carbon atoms, for example, a propenyloxy group, a butenyloxy group, a pentenyloxy group, a hexenyloxy group or the like. The "($C_2$-$C_6$) alkynyloxy group" refers to a straight chain or branched chain alkynyloxy group of 2 to 6 carbon atoms, for example, a propynyloxy group, a butynyloxy group, a pentynyloxy group, a hexynyloxy group or the like.

The "($C_1$-$C_6$) alkylthio group" refers to a straight chain or branched chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, a 1-ethylpropylthio group, a 1-methylbutylthio group, a n-hexylthio group, an isohexylthio group, a 1,1,2-trimethylpropylthio group or the like. The "($C_1$-$C_6$) alkylsulfinyl group" refers to a straight chain or branched chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, a 1-ethylpropylsulfinyl group, a 1-methylbutylsulfinyl group, a n-hexylsulfinyl group, an isohexylsulfinyl group, a 1,1,2-trimethylpropylsulfinyl group or the like. The "($C_1$-$C_6$) alkylsulfonyl group" refers to a straight chain or branched chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, a 1-ethylpropylsulfonyl group, a 1-methylbutylsulfonyl group, a n-hexylsulfonyl group, an isohexylsulfonyl group, a 1,1,2-trimethylpropylsulfonyl group or the like.

The "($C_2$-$C_6$) alkenylthio group" refers to a straight chain or branched chain alkenylthio group of 2 to 6 carbon atoms, for example, a propenylthio group, a butenylthio group, a pentenylthio group, a hexenylthio group or the like. The "($C_2$-$C_6$) alkynylthio group" refers to a straight chain or branched chain alkynylthio group of 2 to 6 carbon atoms, for example, a propynylthio group, a butynylthio group, a pentynylthio group, a hexynylthio group or the like.

The "($C_2$-$C_6$) alkenylsulfinyl group" refers to a straight chain or branched chain alkenylsulfinyl group of 2 to 6 carbon atoms, for example, a propenylsulfinyl group, a butenylsulfinyl group, a pentenylsulfinyl group, a hexenylsulfinyl group or the like. The "($C_2$-$C_6$) alkynylsulfinyl group" refers to a straight chain or branched chain alkynylsulfinyl group of 2 to 6 carbon atoms, for example, a propynylsulfinyl group, a butynylsulfinyl group, a pentynylsulfinyl group, a hexynylsulfinyl group or the like.

The "($C_2$-$C_6$) alkenylsulfonyl group" refers to a straight chain or branched chain alkenylsulfonyl group of 2 to 6 carbon atoms, for example, a propenylsulfonyl group, a butenylsulfonyl group, a pentenylsulfonyl group, a hexenylsulfonyl group or the like. The "($C_2$-$C_6$) alkynylsulfonyl group" refers to a straight chain or branched chain alkynylsulfonyl group of 2 to 6 carbon atoms, for example, a propynylsulfonyl group, a butynylsulfonyl group, a pentynylsulfonyl group, a hexynylsulfonyl group or the like.

The "($C_3$-$C_6$) cycloalkoxy group" refers to a cyclic alkoxy group of 3 to 6 carbon atoms, for example, a cyclopropoxy group, a cyclobutoxy group, a cyclopentyloxy group, a cyclohexyloxy group or the like. The "($C_3$-$C_6$) cycloalkylthio group" refers to a cyclic alkylthio group of 3 to 6 carbon atoms, for example, a cyclopropylthio group, a cyclobutylthio group, a cyclopentylthio group, a cyclohexylthio group or the like. The "($C_3$-$C_6$) cycloalkylsulfinyl group" refers to a cyclic alkylsulfinyl group of 3 to 6 carbon atoms, for example, a cyclopropylsulfinyl group, a cyclobutylsulfinyl group, a cyclopentylsulfinyl group, a cyclohexylsulfinyl group or the like. The "($C_3$-$C_6$) cycloalkylsulfonyl group" refers to a cyclic alkylsulfonyl group of 3 to 6 carbon atoms, for example, a cyclopropylsulfonyl group, a cyclobutylsulfonyl group, a cyclopentylsulfonyl group, a cyclohexylsulfonyl group or the like.

The "phenyl ($C_1$-$C_6$) alkyl group" refers to a group which is the same as the above-described ($C_1$-$C_6$) alkyl group except for having a phenyl group in place of one of the hydrogen atoms, and is for example, a phenylmethyl group (a benzyl group), a phenylethyl group (a phenethyl group), a phenylpropyl group or the like.

The "phenyl ($C_1$-$C_6$) alkyl group having, on the ring, 1 to 5 substituting groups selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group" refers to a group which is the same as the above-described phenyl ($C_1$-$C_6$) alkyl group except that 1 to 5 hydrogen atoms of the phenyl group are independently replaced by any substituting group selected from the group consisting of the above (a) to (g).

The "($C_1$-$C_6$) alkoxycarbonyl group" refers to an alkoxycarbonyl group in which the alkoxy group is the same as the above-described ($C_1$-$C_6$) alkoxy group, i.e., an alkoxycarbonyl group having 2 to 7 carbon atoms, for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group or the like.

The "($C_1$-$C_6$) alkoxycarbonyloxy group" refers to an oxy group having the above-described ($C_1$-$C_6$) alkoxycarbonyl group bound thereto.

The "di-($C_1$-$C_6$) alkylamino group" refers to an amino group di-substituted by the above-described ($C_1$-$C_6$) alkyl groups which may be the same or different, for example, a dimethylamino group, a diethylamino group, an ethylmethylamino group, a dipropylamino group, a methylpropylamino group, a diisopropylamino group or the like.

The "($C_1$-$C_6$) alkylcarbonylthio group" refers to a thio group having a ($C_1$-$C_6$) alkylcarbonyl group bound thereto. The "($C_1$-$C_6$) alkylcarbonyl group" refers to an alkylcarbonyl group in which the alkyl group is the same as the above-described ($C_1$-$C_6$) alkyl group, i.e., an alkylcarbonyl group having 2 to 7 carbon atoms, for example, an acetyl group, a propanoyl group, a butanoyl group, a 2-methylpropanoyl group, a pentanoyl group, a 2-methylbutanoyl group, a 3-methylbutanoyl group, a pivaloyl group, a hexanoyl group, a cyclopropylcarbonyl group or the like.

The "($C_1$-$C_6$) alkylcarbonylamino group" refers to an amino group substituted by a ($C_1$-$C_6$) alkylcarbonyl group. This ($C_1$-$C_6$) alkylcarbonyl group may have the same meaning as the "($C_1$-$C_6$) alkylcarbonyl group" in the above-described "($C_1$-$C_6$) alkylcarbonylthio group."

The "($C_1$-$C_6$) alkylsulfonylamino group" refers to an amino group substituted by the above-described ($C_1$-$C_6$) alkylsulfonyl group.

The "($C_1$-$C_6$) alkylsulfonyl (($C_1$-$C_6$)alkyl)amino group" refers to an amino group substituted by a ($C_1$-$C_6$) alkylsulfonyl group and a ($C_1$-$C_6$) alkyl group. The ($C_1$-$C_6$) alkylsulfonyl group and the ($C_1$-$C_6$) alkyl group may have the same meanings as defined above.

The "tri-($C_1$-$C_6$) alkylsilyl ($C_2$-$C_6$) alkynyl group" refers to a group which is the same as the above-described ($C_2$-$C_6$) alkynyl group except for having a "tri-($C_1$-$C_6$) alkylsilyl group" as a substituting group. The "tri-($C_1$-$C_6$) alkylsilyl group" refers to a silyl group tri-substituted by the above-described ($C_1$-$C_6$) alkyl groups which may be the same or different, and is for example, a trimethylsilyl group, a triethylsilyl group, a tert-butyldimethylsilyl group, an ethyldimethylsilyl group, an isopropyldimethylsilyl group, a n-propyldimethylsilyl group or the like.

The above-mentioned "($C_1$-$C_6$) alkyl group,"
"($C_2$-$C_6$) alkenyl group,"
"($C_2$-$C_6$) alkynyl group,"
"($C_3$-$C_6$) cycloalkyl group,"
"($C_3$-$C_6$) cycloalkoxy group,"
"($C_1$-$C_6$) alkoxy group,"
"($C_2$-$C_6$) alkenyloxy group,"
"($C_2$-$C_6$) alkynyloxy group,"
"($C_1$-$C_6$) alkylthio group,"
"($C_1$-$C_6$) alkylsulfinyl group,"
"($C_1$-$C_6$) alkylsulfonyl group,"

"$(C_2-C_6)$ alkenylthio group,"
"$(C_2-C_6)$ alkynylthio group,"
"$(C_2-C_6)$ alkenylsulfinyl group,"
"$(C_2-C_6)$ alkynylsulfinyl group,"
"$(C_2-C_6)$ alkenylsulfonyl group,"
"$(C_2-C_6)$ alkynylsulfonyl group,"
"$(C_3-C_6)$ cycloalkylthio group,"
"$(C_3-C_6)$ cycloalkylsulfinyl group,"
"$(C_3-C_6)$ cycloalkylsulfonyl group,"
"$(C_1-C_6)$ alkoxycarbonyloxy group,"
"di-$(C_1-C_6)$ alkylamino group" or
"$(C_1-C_6)$ alkylcarbonylthio group"
may be substituted by one or more halogen atoms at a substitutable position(s), and in the case where the above-listed group is substituted by two or more halogen atoms, the halogen atoms may be the same or different.

The above-mentioned "substituting group substituted by one or more halogen atoms at a substitutable position(s)" is expressed as a "halo $(C_1-C_6)$ alkyl group,"
a "halo $(C_2-C_6)$ alkenyl group,"
a "halo $(C_2-C_6)$ alkynyl group,"
a "halo $(C_3-C_6)$ cycloalkyl group,"
a "halo $(C_3-C_6)$ cycloalkoxy group,"
a "halo $(C_1-C_6)$ alkoxy group,"
a "halo $(C_2-C_6)$ alkenyloxy group,"
a "halo $(C_2-C_6)$ alkynyloxy group,"
a "halo $(C_1-C_6)$ alkylthio group,"
a "halo $(C_1-C_6)$ alkylsulfinyl group,"
a "halo $(C_1-C_6)$ alkylsulfonyl group,"
a "halo $(C_2-C_6)$ alkenylthio group,"
a "halo $(C_2-C_6)$ alkynylthio group,"
a "halo $(C_2-C_6)$ alkenylsulfinyl group,"
a "halo $(C_2-C_6)$ alkynylsulfinyl group,"
a "halo $(C_2-C_6)$ alkenylsulfonyl group,"
a "halo $(C_2-C_6)$ alkynylsulfonyl group,"
a "halo $(C_3-C_6)$ cycloalkylthio group,"
a "halo $(C_3-C_6)$ cycloalkylsulfinyl group,"
a "halo $(C_3-C_6)$ cycloalkylsulfonyl group,"
a "halo $(C_1-C_6)$ alkoxycarbonyloxy group,"
a "halo di-$(C_1-C_6)$ alkylamino group" or
a "halo $(C_1-C_6)$ alkylcarbonylthio group."

The expressions "$(C_1-C_6)$," "$(C_2-C_6)$," "$(C_3-C_6)$," etc. each refer to the range of the number of carbon atoms in the substituting groups. The same definition holds true for the groups coupled to the above-mentioned substituting groups, and for example, the "$(C_1-C_6)$ alkoxy $(C_1-C_6)$ alkyl group" means that a straight chain or branched chain alkoxy group of 1 to 6 carbon atoms is bound to a straight chain or branched chain alkyl group of 1 to 6 carbon atoms.

Examples of the salt of the condensed heterocyclic compound represented by the general formula (I) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The condensed heterocyclic compound represented by the general formula (I) of the present invention and a salt thereof can have one or more chiral centers in the structural formula, and can exist as two or more kinds of optical isomers or diastereomers. All the optical isomers and mixtures of the isomers at any ratio are also included in the present invention. Further, the compound represented by the general formula (I) of the present invention and a salt thereof can exist as two kinds of geometric isomers due to a carbon-carbon double bond in the structural formula. All the geometric isomers and mixtures of the isomers at any ratio are also included in the present invention.

In one embodiment of the present invention, preferred are a condensed heterocyclic compound represented by the general formula (I) in which
$R^1$ is a $(C_1-C_6)$ alkyl group;
a $(C_3-C_6)$ cycloalkyl group;
a $(C_2-C_6)$ alkenyl group;
a $(C_2-C_6)$ alkynyl group;
a halo $(C_1-C_6)$ alkyl group;
a $(C_1-C_6)$ alkoxy $(C_1-C_6)$ alkyl group;
a $(C_3-C_6)$ cycloalkyl $(C_1-C_6)$ alkyl group;
a $(C_1-C_6)$ alkylthio $(C_1-C_6)$ alkyl group;
a $(C_1-C_6)$ alkylsulfinyl $(C_1-C_6)$ alkyl group;
a $(C_1-C_6)$ alkylsulfonyl $(C_1-C_6)$ alkyl group;
a cyano $(C_1-C_6)$ alkyl group;
a $(C_1-C_6)$ alkoxycarbonyloxy $(C_1-C_6)$ alkyl group;
a di-$(C_1-C_6)$ alkylamino $(C_1-C_6)$ alkyl group (wherein the alkyl groups of the di-$(C_1-C_6)$ alkylamino moiety may be the same or different);
a phenyl $(C_1-C_6)$ alkyl group; or
a phenyl $(C_1-C_6)$ alkyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group,
$R^2$ is a halogen atom;
a $(C_1-C_6)$ alkyl group;
a $(C_3-C_6)$ cycloalkyl group;
a $(C_2-C_6)$ alkenyl group;
a $(C_2-C_6)$ alkynyl group;
a halo $(C_1-C_6)$ alkyl group;
a $(C_1-C_6)$ alkylthio group;
a halo $(C_1-C_6)$ alkylthio group;
a halo $(C_1-C_6)$ alkylsulfinyl group;
a halo $(C_1-C_6)$ alkylsulfonyl group;
a hydrogen atom;
a $(C_1-C_6)$ alkoxy group;
a halo $(C_1-C_6)$ alkoxy group;
an amino group;
a di-$(C_1-C_6)$ alkylamino group (wherein the alkyl groups of the di-$(C_1-C_6)$ alkyl moiety may be the same or different);
a $(C_1-C_6)$ alkylcarbonyl amino group;
a $(C_1-C_6)$ alkylsulfonylamino group;
a $(C_1-C_6)$ alkylsulfonyl ($(C_1-C_6)$ alkyl)amino group;
a $(C_1-C_6)$ alkoxycarbonyl group; or
a tri-$(C_1-C_6)$ alkylsilyl $(C_2-C_6)$ alkynyl group (wherein the alkyl groups of the tri-$(C_1-C_6)$ alkylsilyl moiety may be the same or different),
$R^3$ is a hydrogen atom,
$R^4$ is a halogen atom;
a $(C_1-C_6)$ alkyl group;
a halo $(C_1-C_6)$ alkyl group;
a mercapto group;
a $(C_1-C_6)$ alkylthio group;
a $(C_1-C_6)$ alkylcarbonylthio group;
a halo $(C_1-C_6)$ alkylthio group;
a phenyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group; or a $(C_1-C_6)$ alkylsulfonyl group,
  $R^5$ is a $(C_1-C_6)$ alkyl group;
a $(C_3-C_6)$ cycloalkyl group;
a halo $(C_1-C_6)$ alkyl group;
a $(C_1-C_6)$ alkoxy $(C_1-C_6)$ alkyl group;
an amino group; or
a $(C_1-C_6)$ alkoxy group,
  $A^1$, $A^2$ and $A^3$ may be the same or different, and each represent a nitrogen atom or a C—$R^6$ group (wherein $R^6$ is (f1) a hydrogen atom), and
  m is 0, 1 or 2, and
a salt thereof.

In one embodiment of the present invention, more preferred are a condensed heterocyclic compound represented by the general formula (I) in which
  $R^1$ is a $(C_1-C_6)$ alkyl group;
a $(C_3-C_6)$ cycloalkyl group;
a $(C_2-C_6)$ alkenyl group;
a halo $(C_1-C_6)$ alkyl group;
a $(C_3-C_6)$ cycloalkyl $(C_1-C_6)$ alkyl group;
a $(C_1-C_6)$ alkylthio $(C_1-C_6)$ alkyl group;
a cyano $(C_1-C_6)$ alkyl group;
a $(C_1-C_6)$ alkoxycarbonyloxy $(C_1-C_6)$ alkyl group;
a di-$(C_1-C_6)$ alkylamino $(C_1-C_6)$ alkyl group (wherein the alkyl groups of the di-$(C_1-C_6)$ alkylamino moiety may be the same or different); or
a phenyl $(C_1-C_6)$ alkyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group,
  $R^2$ is a halogen atom;
a $(C_1-C_6)$ alkyl group;
a $(C_3-C_6)$ cycloalkyl group;
a $(C_2-C_6)$ alkenyl group;
a $(C_2-C_6)$ alkynyl group;
a halo $(C_1-C_6)$ alkyl group;
a $(C_1-C_6)$ alkylthio group;
a halo $(C_1-C_6)$ alkylthio group;
a hydrogen atom;
a halo $(C_1-C_6)$ alkoxy group;
an amino group;
a di-$(C_1-C_6)$ alkylamino group (wherein the alkyl groups of the di-$(C_1-C_6)$ alkyl moiety may be the same or different);
a $(C_1-C_6)$ alkylcarbonyl amino group;
a $(C_1-C_6)$ alkylsulfonylamino group;
a $(C_1-C_6)$ alkylsulfonyl ($(C_1-C_6)$ alkyl) amino group;
a $(C_1-C_6)$ alkoxycarbonyl group; or
a tri-$(C_1-C_6)$ alkylsilyl $(C_2-C_6)$ alkynyl group (wherein the alkyl groups of the tri-$(C_1-C_6)$ alkylsilyl moiety may be the same or different),
  $R^3$ is a hydrogen atom,
  $R^4$ is a halogen atom;
a halo $(C_1-C_6)$ alkyl group;
a mercapto group;
a $(C_1-C_6)$ alkylthio group;
a $(C_1-C_6)$ alkylcarbonylthio group;
a halo $(C_1-C_6)$ alkylthio group;
a phenyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group; or a $(C_1-C_6)$ alkylsulfonyl group,
  $R^5$ is a $(C_1-C_6)$ alkyl group;
a $(C_3-C_6)$ cycloalkyl group; or
a $(C_1-C_6)$ alkoxy $(C_1-C_6)$ alkyl group,
  $A^1$, $A^2$ and $A^3$ may be the same or different, and each represent a nitrogen atom or a C—$R^6$ group (wherein $R^6$ is (f1) a hydrogen atom), and
  m is 0, 1 or 2, and
a salt thereof.

The condensed heterocyclic compound of the present invention or a salt thereof can be produced according to, for example, the production method described below, but the present invention is not limited thereto.

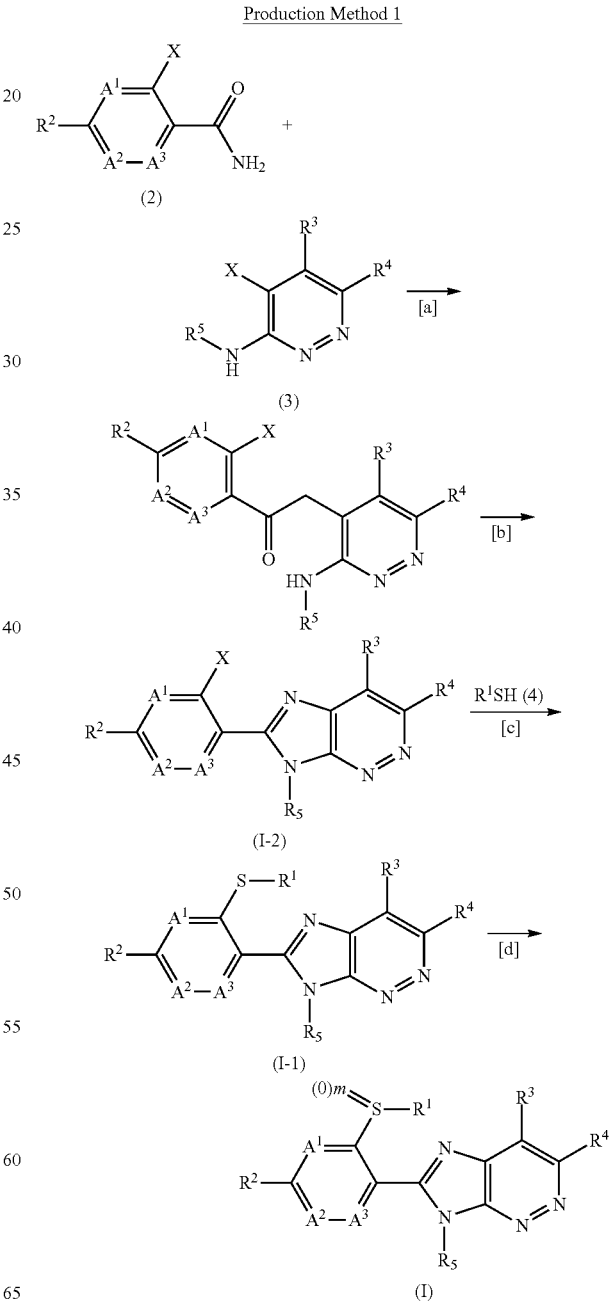

{In the formulae, $R^1$, $R^2$, $R^3$, $R^9$, $R^5$, $A^1$, $A^2$, $A^3$ and m are as defined above, and X represents a halogen atom.}

Production Method at Step [a]

The carboxylic amide compound represented by the general formula (I-3) can be produced by allowing the carboxylic amide represented by the general formula (2) to react with the compound represented by the general formula (3) in the presence of a metal catalyst, abase and an inert solvent. This reaction can be conducted according to the method described in Org. Synth. 78: 23; or Coll. Vol. 10: 423, J. A. C. S. (1999), 121 (18), 4369-4378.

Examples of the metal catalyst that can be used in the present invention include known palladium catalysts such as [1,1'-bis(diphenylphosphino)ferrocene]palladium(II) dichloride, [1,1'-bis(diphenylphosphino)propane]palladium (II) dichloride, [1,1'-bis(diphenylphosphino)butane]palladium(II) dichloride, zerovalent palladium compounds including bis(dibenzylideneacetone)palladium(0) and tris(dibenzylideneacetone)dipalladium(0), palladium(II) acetate, palladium(II) chloride, bis(acetonitrile)palladium (II) dichloride, bis(benzonitrile)palladium(II) dichloride, an allylpalladium(II) chloride dimer and cyclopentadienyl allylpalladium(II). Two or more kinds of these metal catalysts can be used if needed. Usually, the amount of the palladium catalyst used in the present invention is appropriately selected from the range of an about 0.001- to 0.1-fold molar amount relative to the compound represented by the general formula (2).

Examples of the base that can be used in the present invention include hydroxides such as lithium hydroxide, sodium hydroxide, potassium hydroxide and calcium hydroxide; carbonates such as lithium carbonate, lithium hydrogen carbonate, sodium carbonate, sodium hydrogen carbonate, potassium carbonate, potassium hydrogen carbonate, calcium carbonate and magnesium carbonate; acetates such as lithium acetate, sodium acetate and potassium acetate; alkoxides such as sodium methoxide, sodium ethoxide, sodium tert-butoxide and potassium tert-butoxide; metal hydrides such as sodium hydride and potassium hydride; and organic bases such as pyridine, picoline, lutidine, triethylamine, tributylamine and diisopropylethylamine. The amount of the base used is appropriately selected from the range of a 0.5- to 5.0-fold molar amount relative to the compound represented by the general formula (2).

The inert solvent that can be used in this reaction may be any solvent unless it markedly inhibits the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide and 1,3-dimethyl-2-imidazolidinone. These inert solvents may be used alone or as a mixture of two or more kinds.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. After the reaction is completed, the compound of interest is isolated from the post-reaction mixture by a usual method. As needed, the compound of interest can be purified by recrystallization, column chromatography, etc. Alternatively, the product obtained in the reaction may be subjected to the next step without purification or isolation. In some cases, the dehydrating condensation reaction of the next step proceeds at step [a]. In such cases, the next step can be skipped.

Production Method at Step [b]

The condensed heterocyclic compound represented by the general formula (I-2) can be produced by allowing the compound represented by the general formula (I-3) to react in the presence of a condensing agent, a base and an inert solvent.

Examples of the condensing agent used in this reaction include diethyl phosphorocyanidate (DEPC), carbonyldiimidazole (CDI), 1,3-dicyclohexylcarbodiimide (DCC), chlorocarbonic esters and 2-chloro-1-methylpyridinium iodide. The amount of the condensing agent used is appropriately selected from the range of a 1- to 1.5-fold molar amount relative to the compound represented by the general formula (I-2).

Examples of the base used include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethyl aminopyridine. The amount of the base used is usually in the range of a 1- to 10-fold molar amount relative to the compound represented by the general formula (I-2).

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. These inert solvents may be used alone or as a mixture of two or more kinds.

Since this reaction is an equimolar reaction of the reactants, they are basically used in equimolar amounts, but it is possible that any of the reactants is used in an excessive amount. The reaction temperature is in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by a usual method. As needed, the compound of interest can be purified by recrystallization, column chromatography, etc.

Production Method at Step [c]

The condensed heterocyclic compound represented by the general formula (I-1) can be produced by allowing the condensed heterocyclic compound represented by the general formula (I-2) to react with the thiol compound represented by the general formula (4) in the presence of a base in an inert solvent.

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of an about 1- to 5-fold molar amount relative to the compound represented by the general formula (I-2). Commercially available products of sodium methanethiolate or sodium ethanethiolate can also be used as the base, and in this case, compound (4) does not have to be used.

The inert solvent that can be used in this reaction may be any solvent unless it markedly inhibits the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide and 1,3-dimethyl-2-imidazolidinone. These inert solvents may be used alone or as a mixture of two or more kinds.

The reaction temperature in this reaction is usually in the range of about 0° C. to the boiling point of the solvent used.

The reaction time varies with the reaction scale, the reaction temperature and the like, but is basically selected as appropriate from the range of a few minutes to 48 hours. The compound represented by the general formula (4) is usually used in an about 1- to 5-fold molar amount relative to the condensed heterocyclic compound represented by the general formula (I-1). This reaction can be conducted under the atmosphere of an inert gas such as nitrogen gas and argon gas. After the reaction is completed, the compound of interest is isolated from the post-reaction mixture by a usual method. As needed, the compound of interest can be purified by recrystallization, column chromatography, etc.

Production Method at Step [d]

The condensed heterocyclic compound represented by the general formula (I) can be produced by allowing the condensed heterocyclic compound represented by the general formula (I-1) to react with an oxidizing agent in an inert solvent. Examples of the oxidizing agent used in this reaction include peroxides such as a hydrogen peroxide solution, perbenzoic acid and m-chloroperoxybenzoic acid. The amount of the oxidizing agent used is appropriately selected from the range of a 0.8- to 5-fold molar amount relative to the condensed heterocyclic compounds represented by the general formula (I-1), and is preferably in the range of a 1- to 2-fold molar amount.

The inert solvent that can be used in this reaction may be any solvent unless it markedly inhibits the reaction, and the examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. These inert solvents may be used alone or as a mixture of two or more kinds.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by a usual method. As needed, the compound of interest can be purified by recrystallization, column chromatography, etc.

The starting material or the intermediate of the present invention can be produced according to, for example, the following method.

Production Method of Intermediate

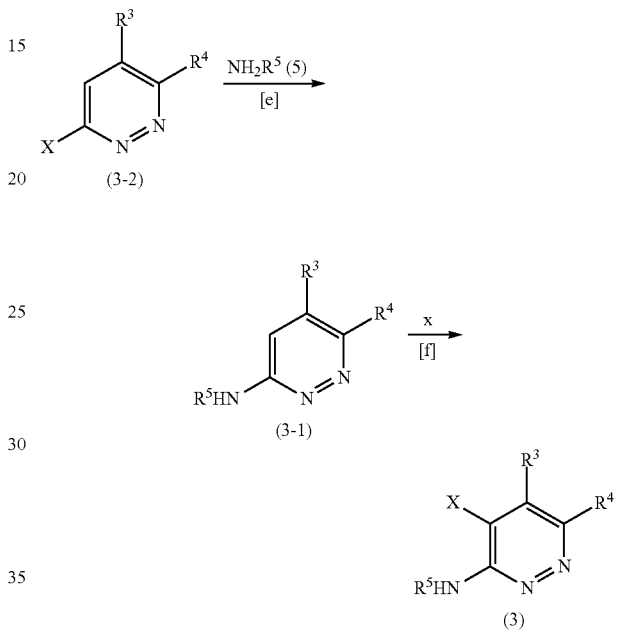

{In the formulae, $R^3$, $R^4$ and $R^5$ are as defined above, and X represents a halogen atom.}

The compound of the general formula (3) can be produced by the following method.

Production Method at Step [e]

The compound represented by the general formula (3-1) can be produced by allowing the compound represented by the general formula (3-2) to react with the amino compound represented by the general formula (5) in an inert solvent. The amount of the amino compound (5) used is appropriately selected from the range of a 1- to 5-fold molar amount relative to compound (3-2).

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and other solvents such as dimethyl sulfoxide and 1,3-dimethyl-2-imidazolidinone. These inert solvents may be used alone or as a mixture of two or more kinds.

If needed, a base may be used, and examples of the base used include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethyl aminopyridine. The amount of the base used is usually in the range of a 1- to 10-fold molar amount relative to the compound represented by the general formula (3-1).

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by a usual method. As needed, the compound of interest can be purified by recrystallization, column chromatography, etc.

Production Method at Step [f]

The compound represented by the general formula (3) can be produced by allowing the compound represented by the general formula (3-1) to react with a halogenating agent in an inert solvent.

The inert solvent that can be used in this reaction may be any solvent unless it markedly inhibits the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; esters such as ethyl acetate; and polar solvents such as N,N-dimethylformamide, N,N-dimethylacetamide, 1,3-dimethyl-2-imidazolidinone, water and acetic acid. These inert solvents may be used alone or as a mixture of two or more kinds.

Examples of the halogenating agent used in the reaction include halogen molecules such as a fluorine, chlorine, bromine or iodine molecule; halosuccinimides such as NCS and NBS; halogenated hydantoins such as DIH; and thionyl chloride.

The reaction temperature in this reaction is appropriately selected from the range of −30° C. to the reflux temperature of the inert solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by a usual method. As needed, the compound of interest can be purified by recrystallization, column chromatography, etc.

Next, specific examples of the compound of the present invention are shown below. In the following table, Me stands for a methyl group, Et stands for an ethyl group, n-Pr stands for a n-propyl group, i-Pr stands for an isopropyl group, c-Pr stands for a cyclopropyl group, Ac stands for an acetyl group, t-Bu stands for a tert-butyl group, Allyl stands for an allyl group, Propargyl stands for a propargyl group (a 2-propynyl group), c-Bu stands for a cyclobutyl group, c-Pent stands for a cyclopentyl group, c-Hex stands for a cyclohexyl group, Ph stands for a phenyl group, and Bn stands for a benzyl group. The physical property refers to a melting point (° C.), a refractive index $n_D$ (measurement temperature; ° C.) or NMR.

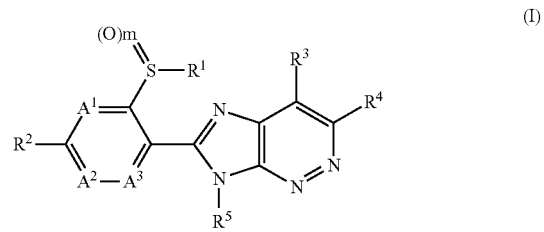

(I)

TABLE 1

| Compound No. | $R^1$ | $R^2$ | $R^4$ | $R^5$ | $A^3$ | m | Physical property |
|---|---|---|---|---|---|---|---|
| 1-1 | Et | $CF_3$ | $CF_3$ | Me | CH | 0 | NMR |
| 1-2 | Et | $CF_3$ | $CF_3$ | Me | CH | 1 | 184-185° C. |
| 1-3 | Et | $CF_3$ | $CF_3$ | Me | CH | 2 | 161-163° C. |
| 1-4 | Et | $CF_3$ | $CF_3$ | Me | N | 0 | 129-131° C. |
| 1-5 | Et | $CF_3$ | $CF_3$ | Me | N | 1 | |
| 1-6 | Et | $CF_3$ | $CF_3$ | Me | N | 2 | 196-197° C. |
| 1-7 | Me | $CF_3$ | $CF_3$ | Me | CH | 0 | 139-141° C. |
| 1-8 | Me | $CF_3$ | $CF_3$ | Me | CH | 1 | 230-232° C. |
| 1-9 | Me | $CF_3$ | $CF_3$ | Me | CH | 2 | 224-226° C. |
| 1-10 | n-Pr | $CF_3$ | $CF_3$ | Me | CH | 0 | 118-119° C. |
| 1-11 | n-Pr | $CF_3$ | $CF_3$ | Me | CH | 1 | |
| 1-12 | n-Pr | $CF_3$ | $CF_3$ | Me | CH | 2 | 132-134° C. |
| 1-13 | i-Pr | $CF_3$ | $CF_3$ | Me | CH | 0 | 88-90° C. |
| 1-14 | i-Pr | $CF_3$ | $CF_3$ | Me | CH | 1 | 183-184° C. |
| 1-15 | i-Pr | $CF_3$ | $CF_3$ | Me | CH | 2 | 150-152° C. |
| 1-16 | Et | $CF_3$ | Cl | Me | CH | 0 | 134-136° C. |
| 1-17 | Et | $CF_3$ | Cl | Me | CH | 1 | 165-167° C. |
| 1-18 | Et | $CF_3$ | Cl | Me | CH | 2 | 186-187° C. |
| 1-19 | Et | $CF_3$ | Me | Me | CH | 0 | |
| 1-20 | Et | $CF_3$ | Me | Me | CH | 1 | |
| 1-21 | Et | $CF_3$ | Me | Me | CH | 2 | |
| 1-22 | Et | $CF_3$ | $CF_3$ | Et | CH | 0 | 126-130° C. |
| 1-23 | Et | $CF_3$ | $CF_3$ | Et | CH | 1 | 158-161° C. |
| 1-24 | Et | $CF_3$ | $CF_3$ | Et | CH | 2 | 164-167° C. |
| 1-25 | Et | $CF_3$ | $CF_3$ | c-Pr | CH | 0 | |
| 1-26 | Et | $CF_3$ | $CF_3$ | c-Pr | CH | 1 | |
| 1-27 | Et | $CF_3$ | $CF_3$ | c-Pr | CH | 2 | |
| 1-28 | Et | Cl | $CF_3$ | Me | CH | 0 | |
| 1-29 | Et | Cl | $CF_3$ | Me | CH | 1 | |
| 1-30 | Et | Cl | $CF_3$ | Me | CH | 2 | 150-152° C. |
| 1-31 | Et | Me | $CF_3$ | Me | CH | 0 | |
| 1-32 | Et | Me | $CF_3$ | Me | CH | 1 | |
| 1-33 | Et | Me | $CF_3$ | Me | CH | 2 | 196-200° C. |
| 1-34 | Et | H | $CF_3$ | Me | CH | 0 | NMR |
| 1-35 | Et | H | $CF_3$ | Me | CH | 1 | NMR |
| 1-36 | Et | H | $CF_3$ | Me | CH | 2 | 194-195° C. |
| 1-37 | Et | $CF_2CF_3$ | $CF_3$ | Me | CH | 0 | NMR |
| 1-38 | Et | $CF_2CF_3$ | $CF_3$ | Me | CH | 1 | |
| 1-39 | Et | $CF_2CF_3$ | $CF_3$ | Me | CH | 2 | 163-165° C. |
| 1-40 | Et | $CF_2CF_3$ | $CF_3$ | Me | N | 0 | NMR |
| 1-41 | Et | $CF_2CF_3$ | $CF_3$ | Me | N | 1 | |
| 1-42 | Et | $CF_2CF_3$ | $CF_3$ | Me | N | 2 | 193-194° C. |
| 1-43 | Me | $CF_2CF_3$ | $CF_3$ | Me | CH | 0 | |
| 1-44 | Me | $CF_2CF_3$ | $CF_3$ | Me | CH | 1 | |
| 1-45 | Me | $CF_2CF_3$ | $CF_3$ | Me | CH | 2 | |
| 1-46 | n-Pr | $CF_2CF_3$ | $CF_3$ | Me | CH | 0 | |
| 1-47 | n-Pr | $CF_2CF_3$ | $CF_3$ | Me | CH | 1 | |
| 1-48 | n-Pr | $CF_2CF_3$ | $CF_3$ | Me | CH | 2 | |
| 1-49 | i-Pr | $CF_2CF_3$ | $CF_3$ | Me | CH | 0 | |
| 1-50 | i-Pr | $CF_2CF_3$ | $CF_3$ | Me | CH | 1 | |
| 1-51 | i-Pr | $CF_2CF_3$ | $CF_3$ | Me | CH | 2 | |
| 1-52 | Et | $CF_2CF_3$ | Cl | Me | CH | 0 | |
| 1-53 | Et | $CF_2CF_3$ | Cl | Me | CH | 1 | |
| 1-54 | Et | $CF_2CF_3$ | Cl | Me | CH | 2 | |
| 1-55 | Et | $CF_2CF_3$ | Me | Me | CH | 0 | |
| 1-56 | Et | $CF_2CF_3$ | Me | Me | CH | 1 | |
| 1-57 | Et | $CF_2CF_3$ | Me | Me | CH | 2 | |
| 1-58 | Et | $CF_2CF_3$ | $CF_3$ | Et | CH | 0 | |
| 1-59 | Et | $CF_2CF_3$ | $CF_3$ | Et | CH | 1 | |
| 1-60 | Et | $CF_2CF_3$ | $CF_3$ | Et | CH | 2 | |
| 1-61 | Et | $CF_3$ | $CF_2CF_3$ | Me | CH | 0 | 97-100° C. |
| 1-62 | Et | $CF_3$ | $CF_2CF_3$ | Me | CH | 1 | 195-197° C. |

TABLE 1-continued

| | | | | | | | |
|---|---|---|---|---|---|---|---|
| 1-63 | Et | CF$_3$ | CF$_2$CF$_3$ | Me | CH | 2 | 191-192° C. |
| 1-64 | Et | CF(CF$_3$)$_2$ | CF$_3$ | Me | CH | 0 | 95-97° C. |
| 1-65 | Et | CF(CF$_3$)$_2$ | CF$_3$ | Me | CH | 1 | |
| 1-66 | Et | CF(CF$_3$)$_2$ | CF$_3$ | Me | CH | 2 | 191-193° C. |

NMR Data

| Compound No. | $^1$H-NMR (CDCl$_3$) |
|---|---|
| 1-1 | 8.20(s, 1H), 7.75(s, 1H), 7.64(d, 2H), 3.99(s, 3H), 3.00(dd, 2H), 1.26(t, 3H) |
| 1-34 | 8.17(s, 1H), 8.61-7.54(m, 2H), 7.47(dd, 1H), 7.41(dt, 2H), 3.96(s, 3H), 2.90(dd, 2H), 1.24(t, 3H) |
| 1-35 | 8.29(dd, 1H), 8.18(d, 1H), 8.15(dd, 1H), 7.90(dt, 1H), 7.75(dt, 1H), 7.66(dd, 1H), 4.10(s, 3H), 3.42-3.32(m, 1H), 3.05-2.95(m, 1H), 1.32(t, 3H) |
| 1-37 | 8.21(s, 1H), 7.70(s, 1H), 7.03(s, 2H), 4.00(s, 3H), 2.97(dd, 2H), 1.30(t, 3H) |
| 1-40 | 8.75(d, 1H), 8.29(s, 1H), 7.95(d, 1H), 4.32(s, 3H), 3.04(dd, 2H), 1.40(t, 3H) |
| 3-2 | 8.74(s, 1H), 8.25(s, 1H), 8.15(d, 1H), 8.09(d, 1H), 4.30(s, 3H) |
| 3-27 | 8.48(s, 1H), 8.20(s, 1H), 8.13(d, 1H), 7.74(d, 1H), 3.91(s, 3H), 3.52(dd, 2H), 2.73(t, 1H), 2.04(dd, 2H), 1.94(dd, 2H), 1.76(dd, 2H) |
| 3-65 | 8.78(s, 1H), 8.25(s, 1H), 8.14(d, 1H), 8.04(d, 1H), 4.62(d, 1H), 4.43(d, 1H), 4.29(s, 3H) |
| 7-61 | 8.18(s, 1H), 7.58(m, 2H), 7.44(m, 2H), 3.97(s, 3H), 2.91(dd, 2H), 1.25(t, 3H) |
| 7-63 | 8.25(m, 1H), 8.15(s, 1H), 7.89(m, 2H), 7.59(m, 1H), 3.91(s, 3H), 3.39(dd, 2H), 1.25(t, 3H) |

In the compounds shown in Table 1, R$^3$ is H, and A$^1$ and A$^2$ are each CH.

TABLE 2

| Compound No. | R$^1$ | R$^2$ | R$^4$ | R$^5$ | A$^3$ | m | Physical property |
|---|---|---|---|---|---|---|---|
| 2-1 | Et | CF$_3$ | CF$_3$ | n-Pr | CH | 0 | 90-92° C. |
| 2-2 | Et | CF$_3$ | CF$_3$ | n-Pr | CH | 1 | 174-177° C. |
| 2-3 | Et | CF$_3$ | CF$_3$ | n-Pr | CH | 2 | 173-175° C. |
| 2-4 | Et | CF$_3$ | CF$_3$ | i-Pr | CH | 0 | |
| 2-5 | Et | CF$_3$ | CF$_3$ | i-Pr | CH | 1 | |
| 2-6 | Et | CF$_3$ | CF$_3$ | i-Pr | CH | 2 | |
| 2-7 | Et | CF$_3$ | CF$_3$ | CH$_2$CF$_3$ | CH | 0 | |
| 2-8 | Et | CF$_3$ | CF$_3$ | CH$_2$CF$_3$ | CH | 1 | |
| 2-9 | Et | CF$_3$ | CF$_3$ | CH$_2$CF$_3$ | CH | 2 | |
| 2-10 | Et | CF$_3$ | CF$_3$ | CH$_2$CH$_2$OCH$_3$ | CH | 0 | 88-90° C. |
| 2-11 | Et | CF$_3$ | CF$_3$ | CH$_2$CH$_2$OCH$_3$ | CH | 1 | 132-135° C. |
| 2-12 | Et | CF$_3$ | CF$_3$ | CH$_2$CH$_2$OCH$_3$ | CH | 2 | 67-69° C. |
| 2-13 | Et | CF$_3$ | CF$_3$ | OMe | CH | 0 | |
| 2-14 | Et | CF$_3$ | CF$_3$ | OMe | CH | 1 | |
| 2-15 | Et | CF$_3$ | CF$_3$ | OMe | CH | 2 | |
| 2-16 | Et | CF$_3$ | CF$_3$ | NH$_2$ | CH | 0 | |
| 2-17 | Et | CF$_3$ | CF$_3$ | NH$_2$ | CH | 1 | |
| 2-18 | Et | CF$_3$ | CF$_3$ | NH$_2$ | CH | 2 | |

In the compounds shown in Table 2, R$^3$ is H, and A$^1$ and A$^2$ are each CH.

TABLE 3

| Compound No. | R$^1$ | R$^2$ | R$^4$ | R$^5$ | A$^3$ | m | Physical property |
|---|---|---|---|---|---|---|---|
| 3-1 | CF$_3$ | CF$_3$ | CF$_3$ | Me | CH | 0 | 124-125° C. |
| 3-2 | CF$_3$ | CF$_3$ | CF$_3$ | Me | CH | 1 | NMR |
| 3-3 | CF$_3$ | CF$_3$ | CF$_3$ | Me | CH | 2 | 131-132° C. |
| 3-4 | CF$_3$ | CF$_3$ | CF$_3$ | Me | CH | 0 | |
| 3-5 | CH$_2$CHF$_2$ | CF$_3$ | CF$_3$ | Me | CH | 1 | |
| 3-6 | CH$_2$CHF$_2$ | CF$_3$ | CF$_3$ | Me | CH | 2 | |
| 3-7 | CH$_2$CF$_3$ | CF$_3$ | CF$_3$ | Me | CH | 0 | 106-108° C. |
| 3-8 | CH$_2$CF$_3$ | CF$_3$ | CF$_3$ | Me | CH | 1 | 222-224° C. |
| 3-9 | CH$_2$CF$_3$ | CF$_3$ | CF$_3$ | Me | CH | 2 | 167-169° C. |
| 3-10 | c-Pr | CF$_3$ | CF$_3$ | Me | CH | 0 | |
| 3-11 | c-Pr | CF$_3$ | CF$_3$ | Me | CH | 1 | |
| 3-12 | c-Pr | CF$_3$ | CF$_3$ | Me | CH | 2 | |
| 3-13 | c-Bu | CF$_3$ | CF$_3$ | Me | CH | 0 | |
| 3-14 | c-Bu | CF$_3$ | CF$_3$ | Me | CH | 1 | |
| 3-15 | c-Bu | CF$_3$ | CF$_3$ | Me | CH | 2 | |
| 3-16 | c-Pent | CF$_3$ | CF$_3$ | Me | CH | 0 | |
| 3-17 | c-Pent | CF$_3$ | CF$_3$ | Me | CH | 1 | |
| 3-18 | c-Pent | CF$_3$ | CF$_3$ | Me | CH | 2 | |
| 3-19 | c-Hex | CF$_3$ | CF$_3$ | Me | CH | 0 | 134-136° C. |
| 3-20 | c-Hex | CF$_3$ | CF$_3$ | Me | CH | 1 | 192-194° C. |
| 3-21 | c-Hex | CF$_3$ | CF$_3$ | Me | CH | 2 | 155-156° C. |
| 3-22 | CH$_2$—c-Pr | CF$_3$ | CF$_3$ | Me | CH | 0 | |
| 3-23 | CH$_2$—c-Pr | CF$_3$ | CF$_3$ | Me | CH | 1 | |
| 3-24 | CH$_2$—c-Pr | CF$_3$ | CF$_3$ | Me | CH | 2 | |
| 3-25 | CH$_2$—c-Bu | CF$_3$ | CF$_3$ | Me | CH | 0 | 135-137° C. |
| 3-26 | CH$_2$—c-Bu | CF$_3$ | CF$_3$ | Me | CH | 1 | |
| 3-27 | CH$_2$—c-Bu | CF$_3$ | CF$_3$ | Me | CH | 2 | NMR |
| 3-28 | CH$_2$—c-Pent | CF$_3$ | CF$_3$ | Me | CH | 0 | |
| 3-29 | CH$_2$—c-Pent | CF$_3$ | CF$_3$ | Me | CH | 1 | |
| 3-30 | CH$_2$—c-Pent | CF$_3$ | CF$_3$ | Me | CH | 2 | |
| 3-31 | Allyl | CF$_3$ | CF$_3$ | Me | CH | 0 | 1.551(21° C.) |
| 3-32 | Allyl | CF$_3$ | CF$_3$ | Me | CH | 1 | |
| 3-33 | Allyl | CF$_3$ | CF$_3$ | Me | CH | 2 | |
| 3-34 | Propargyl | CF$_3$ | CF$_3$ | Me | CH | 0 | |
| 3-35 | Propargyl | CF$_3$ | CF$_3$ | Me | CH | 1 | |
| 3-36 | Propargyl | CF$_3$ | CF$_3$ | Me | CH | 2 | |
| 3-37 | Bn | CF$_3$ | CF$_3$ | Me | CH | 0 | |
| 3-38 | Bn | CF$_3$ | CF$_3$ | Me | CH | 1 | |
| 3-39 | Bn | CF$_3$ | CF$_3$ | Me | CH | 2 | |
| 3-40 | 4-Cl-Bn | CF$_3$ | CF$_3$ | Me | CH | 0 | 139-141° C. |
| 3-41 | 4-Cl-Bn | CF$_3$ | CF$_3$ | Me | CH | 1 | 214-216° C. |

TABLE 3-continued

| Compound No. | R¹ | R² | R⁴ | R⁵ | A³ | m | Physical property |
|---|---|---|---|---|---|---|---|
| 3-42 | 4-Cl-Bn | $CF_3$ | $CF_3$ | Me | CH | 2 | 184-185° C. |
| 3-43 | $CH_2CH_2OCH_3$ | $CF_3$ | $CF_3$ | Me | CH | 0 | |
| 3-44 | $CH_2CH_2OCH_3$ | $CF_3$ | $CF_3$ | Me | CH | 1 | |
| 3-45 | $CH_2CH_2OCH_3$ | $CF_3$ | $CF_3$ | Me | CH | 2 | |
| 3-46 | $CH_2CH_2N(CH_3)_2$ | $CF_3$ | $CF_3$ | Me | CH | 0 | 59-61° C. |
| 3-47 | $CH_2CH_2N(CH_3)_2$ | $CF_3$ | $CF_3$ | Me | CH | 1 | |
| 3-48 | $CH_2CH_2N(CH_3)_2$ | $CF_3$ | $CF_3$ | Me | CH | 2 | |
| 3-49 | $CH_2OCH_3$ | $CF_3$ | $CF_3$ | Me | CH | 0 | |
| 3-50 | $CH_2OCH_3$ | $CF_3$ | $CF_3$ | Me | CH | 1 | |
| 3-51 | $CH_2OCH_3$ | $CF_3$ | $CF_3$ | Me | CH | 2 | |
| 3-52 | $CH_2SCH_3$ | $CF_3$ | $CF_3$ | Me | CH | 0 | 93-94° C. |
| 3-53 | $CH_2SCH_3$ | $CF_3$ | $CF_3$ | Me | CH | 1 | |
| 3-54 | $CH_2SCH_3$ | $CF_3$ | $CF_3$ | Me | CH | 2 | |
| 3-55 | $CH_2SOCH_3$ | $CF_3$ | $CF_3$ | Me | CH | 0 | |
| 3-56 | $CH_2SOCH_3$ | $CF_3$ | $CF_3$ | Me | CH | 1 | |
| 3-57 | $CH_2SOCH_3$ | $CF_3$ | $CF_3$ | Me | CH | 2 | |
| 3-58 | $CH_2SO_2CH_3$ | $CF_3$ | $CF_3$ | Me | CH | 0 | |
| 3-59 | $CH_2SO_2CH_3$ | $CF_3$ | $CF_3$ | Me | CH | 1 | |
| 3-60 | $CH_2SO_2CH_3$ | $CF_3$ | $CF_3$ | Me | CH | 2 | |
| 3-61 | $CH_2OCO_2CH_3$ | $CF_3$ | $CF_3$ | Me | CH | 0 | 1.542(18° C.) |
| 3-62 | $CH_2OCO_2CH_3$ | $CF_3$ | $CF_3$ | Me | CH | 1 | 195-196° C. |
| 3-63 | $CH_2OCO_2CH_3$ | $CF_3$ | $CF_3$ | Me | CH | 2 | 187-189° C. |
| 3-64 | $CH_2CN$ | $CF_3$ | $CF_3$ | Me | CH | 0 | 1.5429(29° C.) |
| 3-65 | $CH_2CN$ | $CF_3$ | $CF_3$ | Me | CH | 1 | NMR |
| 3-66 | $CH_2CN$ | $CF_3$ | $CF_3$ | Me | CH | 2 | |

In the compounds shown in Table 3, $R^3$ is H, and $A^1$ and $A^2$ are each CH.

TABLE 4

| Compound No. | R¹ | R² | R⁴ | R⁵ | A³ | m | Physical property |
|---|---|---|---|---|---|---|---|
| 4-1 | Et | $OCF_3$ | $CF_3$ | Me | CH | 0 | 117-119° C. |
| 4-2 | Et | $OCF_3$ | $CF_3$ | Me | CH | 1 | 172-174° C. |
| 4-3 | Et | $OCF_3$ | $CF_3$ | Me | CH | 2 | 174-176° C. |
| 4-4 | Et | $SCF_3$ | $CF_3$ | Me | CH | 0 | 108-110° C. |
| 4-5 | Et | $SCF_3$ | $CF_3$ | Me | CH | 1 | 154-155° C. |
| 4-6 | Et | $SCF_3$ | $CF_3$ | Me | CH | 2 | 128-130° C. |
| 4-7 | Et | Br | $CF_3$ | Me | CH | 0 | |
| 4-8 | Et | Br | $CF_3$ | Me | CH | 1 | |
| 4-9 | Et | Br | $CF_3$ | Me | CH | 2 | 202-204° C. |
| 4-10 | Et | I | $CF_3$ | Me | CH | 0 | |
| 4-11 | Et | I | $CF_3$ | Me | CH | 1 | |
| 4-12 | Et | I | $CF_3$ | Me | CH | 2 | 233-235° C. |
| 4-13 | Et | F | $CF_3$ | Me | CH | 0 | |
| 4-14 | Et | F | $CF_3$ | Me | CH | 1 | |
| 4-15 | Et | F | $CF_3$ | Me | CH | 2 | 191-195° C. |
| 4-16 | Et | $SCH_3$ | $CF_3$ | Me | CH | 0 | |
| 4-17 | Et | $SCH_3$ | $CF_3$ | Me | CH | 1 | |
| 4-18 | Et | $SCH_3$ | $CF_3$ | Me | CH | 2 | 158-160° C. |
| 4-19 | Et | S—i-Pr | $CF_3$ | Me | CH | 0 | |
| 4-20 | Et | S—i-Pr | $CF_3$ | Me | CH | 1 | |
| 4-21 | Et | S—i-Pr | $CF_3$ | Me | CH | 2 | 147-150° C. |
| 4-22 | Et | $SCH_2CF_3$ | $CF_3$ | Me | CH | 0 | |
| 4-23 | Et | $SCH_2CF_3$ | $CF_3$ | Me | CH | 1 | |
| 4-24 | Et | $SCH_2CF_3$ | $CF_3$ | Me | CH | 2 | |
| 4-25 | Et | $OCH_3$ | $CF_3$ | Me | CH | 0 | |
| 4-26 | Et | $OCH_3$ | $CF_3$ | Me | CH | 1 | |
| 4-27 | Et | $OCH_3$ | $CF_3$ | Me | CH | 2 | |
| 4-28 | Et | O—i-Pr | $CF_3$ | Me | CH | 0 | |
| 4-29 | Et | O—i-Pr | $CF_3$ | Me | CH | 1 | |
| 4-30 | Et | O—i-Pr | $CF_3$ | Me | CH | 2 | |
| 4-31 | Et | $OCH_2CF_3$ | $CF_3$ | Me | CH | 0 | |
| 4-32 | Et | $OCH_2CF_3$ | $CF_3$ | Me | CH | 1 | |
| 4-33 | Et | $OCH_2CF_3$ | $CF_3$ | Me | CH | 2 | |
| 4-34 | Et | $NH_2$ | $CF_3$ | Me | CH | 0 | |
| 4-35 | Et | $NH_2$ | $CF_3$ | Me | CH | 1 | |
| 4-36 | Et | $NH_2$ | $CF_3$ | Me | CH | 2 | 276-279° C. |

In the compounds shown in Table 4, $R^3$ is H, and $A^1$ and $A^2$ are each CH.

TABLE 5

| Compound No. | R¹ | R² | R⁴ | R⁵ | A³ | m | Physical property |
|---|---|---|---|---|---|---|---|
| 5-1 | Et | H | $CF_2CF_3$ | Me | CH | 0 | 1.562(18° C.) |
| 5-2 | Et | H | $CF_2CF_3$ | Me | CH | 1 | |
| 5-3 | Et | H | $CF_2CF_3$ | Me | CH | 2 | 137-139° C. |
| 5-4 | Et | H | $CF_2CF_3$ | Me | N | 0 | |
| 5-5 | Et | H | $CF_2CF_3$ | Me | N | 1 | |
| 5-6 | Et | H | $CF_2CF_3$ | Me | N | 2 | |
| 5-7 | Et | $CF_3$ | $SCF_3$ | Me | CH | 0 | 132.5-133° C. |
| 5-8 | Et | $CF_3$ | $SCF_3$ | Me | CH | 2 | 163-165° C. |
| 5-9 | Et | $CF_3$ | Br | Me | CH | 0 | 79-80° C. |
| 5-10 | Et | $CF_3$ | Br | Me | CH | 2 | 180-182° C. |
| 5-11 | Et | $CF_3$ | SAc | Me | CH | 0 | 118.5-120° C. |
| 5-12 | Et | $CF_3$ | SH | Me | CH | 0 | 230-233° C. |
| 5-13 | Et | $CF_3$ | S—t-Bu | Me | CH | 0 | 1.5892(21° C.) |
| 5-14 | Et | $CF_3$ | S—t-Bu | Me | CH | 2 | 170-171° C. |
| 5-15 | Et | $CF_3$ | 4-$CF_3$Ph | Me | CH | 0 | 181-184° C. |
| 5-16 | Et | $CF_3$ | 4-$CF_3$Ph | Me | CH | 2 | 250-251° C. |
| 5-17 | Et | $CF_3$ | $(CF_2)_3CF_3$ | Me | CH | 0 | 1.5025(18.9) |
| 5-18 | Et | $CF_3$ | $(CF_2)_3CF_3$ | Me | CH | 1 | 196-197 |
| 5-19 | Et | $CF_3$ | $(CF_2)_3CF_3$ | Me | CH | 2 | 80-83 |

In the compounds shown in Table 5, $R^3$ is H, and $A^1$ and $A^2$ are each CH.

TABLE 6

| Compound No. | R¹ | R² | R⁴ | R⁵ | A³ | m | Physical property |
|---|---|---|---|---|---|---|---|
| 6-1 | Et | $CF_3$ | $CF_3$ | c-Pent | CH | 0 | 176-180° C. |
| 6-2 | Et | $CF_3$ | $CF_3$ | c-Pent | CH | 1 | 80-83° C. |

TABLE 6-continued

| Compound No. | $R^1$ | $R^2$ | $R^4$ | $R^5$ | $A^3$ | m | Physical property |
|---|---|---|---|---|---|---|---|
| 6-3 | Et | $CF_3$ | $CF_3$ | c-Pent | CH | 2 | 100-103° C. |
| 6-4 | Et | n-Pr | $CF_3$ | Me | CH | 2 | 162-164° C. |
| 6-5 | Et | c-Pr | $CF_3$ | Me | CH | 2 | 172-173° C. |
| 6-6 | Et | i-Pr | $CF_3$ | Me | CH | 2 | 177-178° C. |
| 6-7 | Et | $NHSO_2Me$ | $CF_3$ | Me | CH | 2 | 266-268° C. |
| 6-8 | Et | NHAc | $CF_3$ | Me | CH | 2 | 222-224° C. |
| 6-9 | Et | $N(Me)SO_2Me$ | $CF_3$ | Me | CH | 2 | 189-190° C. |
| 6-10 | Et | $CO_2Et$ | $CF_3$ | Me | CH | 2 | 156-157° C. |
| 6-11 | Et | $NMe_2$ | $CF_3$ | Me | CH | 2 | 186-187° C. |
| 6-12 | Et | C≡CH | $CF_3$ | Me | CH | 2 | 205-206° C. |
| 6-13 | Et | $C≡CSi(Me)_3$ | $CF_3$ | Me | CH | 2 | 174-177° C. |
| 6-14 | Et | $CH=CH_2$ | $CF_3$ | Me | CH | 2 | 179-180° C. |
| 6-15 | Et | $CF_3$ | $SO_2$—t-Bu | Me | N | 2 | 104-108° C. |

In the compounds shown in Table 6, $R^3$ is H, and $A^1$ and $A^2$ are each CH.

TABLE 7

| Compound No. | $R^1$ | $R^2$ | $R^4$ | $R^5$ | $A^3$ | m | Physical property |
|---|---|---|---|---|---|---|---|
| 7-1 | Et | H | $CF_2CF_3$ | Me | N | 0 | |
| 7-2 | Et | H | $CF_2CF_3$ | Me | N | 1 | |
| 7-3 | Et | H | $CF_2CF_3$ | Me | N | 0 | |
| 7-4 | Et | $CF_3$ | $CF_2CF_3$ | Me | N | 0 | |
| 7-5 | Et | $CF_3$ | $CF_2CF_3$ | Me | N | 1 | |
| 7-6 | Et | $CF_3$ | $CF_2CF_3$ | Me | N | 2 | |
| 7-7 | Et | $CF_2CF_3$ | $CF_2CF_3$ | Me | N | 1 | |
| 7-8 | Et | $CF_2CF_3$ | $CF_2CF_3$ | Me | N | 1 | |
| 7-9 | Et | $CF_2CF_3$ | $CF_2CF_3$ | Me | N | 2 | |
| 7-10 | Et | $SCF_3$ | $CF_2CF_3$ | Me | N | 0 | |
| 7-11 | Et | $SCF_3$ | $CF_2CF_3$ | Me | N | 1 | |
| 7-12 | Et | $SCF_3$ | $CF_2CF_3$ | Me | N | 2 | |
| 7-13 | Et | H | $SCF_3$ | Me | N | 0 | |
| 7-14 | Et | H | $SCF_3$ | Me | N | 1 | |
| 7-15 | Et | H | $SCF_3$ | Me | N | 2 | |
| 7-16 | Et | $CF_3$ | $SCF_3$ | Me | N | 0 | |
| 7-17 | Et | $CF_3$ | $SCF_3$ | Me | N | 1 | |
| 7-18 | Et | $CF_3$ | $SCF_3$ | Me | N | 2 | |
| 7-19 | Et | $CF_2CF_3$ | $SCF_3$ | Me | N | 1 | |
| 7-20 | Et | $CF_2CF_3$ | $SCF_3$ | Me | N | 1 | |
| 7-21 | Et | $CF_2CF_3$ | $SCF_3$ | Me | N | 2 | |
| 7-22 | Et | $SCF_3$ | $SCF_3$ | Me | N | 0 | |
| 7-23 | Et | $SCF_3$ | $SCF_3$ | Me | N | 1 | |
| 7-24 | Et | $SCF_3$ | $SCF_3$ | Me | N | 2 | |
| 7-25 | Et | $CF_2CF_3$ | $CF_2CF_3$ | Me | CH | 0 | |
| 7-26 | Et | $CF_2CF_3$ | $CF_2CF_3$ | Me | CH | 1 | |
| 7-27 | Et | $CF_2CF_3$ | $CF_2CF_3$ | Me | CH | 2 | |
| 7-28 | Et | $SCF_3$ | $CF_2CF_3$ | Me | CH | 0 | |
| 7-29 | Et | $SCF_3$ | $CF_2CF_3$ | Me | CH | 1 | |
| 7-30 | Et | $SCF_3$ | $CF_2CF_3$ | Me | CH | 2 | |
| 7-31 | Et | $SOCF_3$ | $CF_2CF_3$ | Me | CH | 0 | |
| 7-32 | Et | $SOCF_3$ | $CF_2CF_3$ | Me | CH | 1 | |
| 7-33 | Et | $SOCF_3$ | $CF_2CF_3$ | Me | CH | 2 | |
| 7-34 | Et | $SO_2CF_3$ | $CF_2CF_3$ | Me | CH | 0 | |
| 7-35 | Et | $SO_2CF_3$ | $CF_2CF_3$ | Me | CH | 1 | |
| 7-36 | Et | $SO_2CF_3$ | $CF_2CF_3$ | Me | CH | 2 | |
| 7-37 | Et | $OCF_3$ | $CF_2CF_3$ | Me | CH | 0 | |
| 7-38 | Et | $OCF_3$ | $CF_2CF_3$ | Me | CH | 1 | |
| 7-39 | Et | $OCF_3$ | $CF_2CF_3$ | Me | CH | 2 | |
| 7-40 | Et | I | $CF_2CF_3$ | Me | CH | 0 | |
| 7-41 | Et | I | $CF_2CF_3$ | Me | CH | 1 | |
| 7-42 | Et | I | $CF_2CF_3$ | Me | CH | 2 | |
| 7-43 | Et | $CF_2CF_3$ | $SCF_3$ | Me | CH | 0 | |
| 7-44 | Et | $CF_2CF_3$ | $SCF_3$ | Me | CH | 1 | |
| 7-45 | Et | $CF_2CF_3$ | $SCF_3$ | Me | CH | 2 | |
| 7-46 | Et | $SCF_3$ | $SCF_3$ | Me | CH | 1 | |
| 7-47 | Et | $SCF_3$ | $SCF_3$ | Me | CH | 1 | |
| 7-48 | Et | $SCF_3$ | $SCF_3$ | Me | CH | 2 | |
| 7-49 | Et | $SOCF_3$ | $SCF_3$ | Me | CH | 0 | |
| 7-50 | Et | $SOCF_3$ | $SCF_3$ | Me | CH | 1 | |
| 7-51 | Et | $SOCF_3$ | $SCF_3$ | Me | CH | 2 | |
| 7-52 | Et | $SO_2CF_3$ | $SCF_3$ | Me | CH | 0 | |
| 7-53 | Et | $SO_2CF_3$ | $SCF_3$ | Me | CH | 1 | |
| 7-54 | Et | $SO_2CF_3$ | $SCF_3$ | Me | CH | 2 | |
| 7-55 | Et | $OCF_3$ | $SCF_3$ | Me | CH | 0 | |
| 7-56 | Et | $OCF_3$ | $SCF_3$ | Me | CH | 1 | |
| 7-57 | Et | $OCF_3$ | $SCF_3$ | Me | CH | 2 | |
| 7-58 | Et | I | $SCF_3$ | Me | CH | 0 | |
| 7-59 | Et | I | $SCF_3$ | Me | CH | 1 | |
| 7-60 | Et | I | $SCF_3$ | Me | CH | 2 | |
| 7-61 | Et | H | $CF_2CF_2CF_3$ | Me | CH | 0 | NMR |
| 7-62 | Et | H | $CF_2CF_2CF_3$ | Me | CH | 1 | |
| 7-63 | Et | H | $CF_2CF_2CF_3$ | Me | CH | 2 | NMR |

In the compounds shown in Table 7, $R^3$ is H, and $A^1$ and $A^2$ are each CH.

The agricultural and horticultural insecticide comprising the condensed heterocyclic compound represented by the general formula (I) of the present invention or a salt thereof as an active ingredient is suitable for controlling a variety of insect pests which may damage paddy rice, fruit trees, vegetables, other crops and ornamental flowering plants. The insect pests to be controlled are, for example, agricultural and forest pests, horticultural pests, stored grain pests, sanitary pests, nematodes, etc.

Specific examples of the pests, nematodes, etc. include the following:

the species of the order Lepidoptera such as *Parasa consocia*, *Anomis mesogona*, *Papilio xuthus*, *Matsumuraeses azukivora*, *Ostrinia scapulalis*, *Spodoptera exempta*, *Hyphantria cunea*, *Ostrinia furnacalis*, *Pseudaletia separata*, *Tinea translucens*, *Bactra furfurana*, *Parnara guttata*, *Marasmia exigua*, *Parnara guttata*, *Sesamia inferens*, *Brachmia triannulella*, *Monema flavescens*, *Trichoplusia ni*, *Pleuroptya ruralis*, *Cystidia couaggaria*, *Lampides boeticus*, *Cephonodes hylas*, *Helicoverpa armigera*, *Phalerodonta manleyi*, *Eumeta japonica*, *Pieris brassicae*, *Malacosoma neustria testacea*, *Stathmopoda masinissa*, *Cuphodes diospyrosella*, *Archips xylosteanus*, *Agrotis segetum*, *Tetramoera schistaceana*, *Papilio machaon hippocrates*, *Endoclyta sinensis*, *Lyonetia prunifoliella*, *Phyllonorycter ringoneella*, *Cydia kurokoi*, *Eucoenogenes aestuosa*, *Lobesia botrana*, *Latoia sinica*, *Euzophera batangensis*, *Phalonidia mesotypa*, *Spilosoma imparilis*, *Glyphodes pyloalis*, *Olethreutes mori*, *Tineola bisselliella*, *Endoclyta excrescens*, *Nemapogon granellus*, *Synanthedon hector*, *Cydia pomonella*, *Plutella xylostella*, *Cnaphalocrocis medinalis*, *Sesamia calamistis*, *Scirpophaga incertulas*, *Pediasia teterrellus*, *Phthorimaea operculella*, *Stauropus fagi persimilis*, *Etiella zinckenella*, *Spodoptera exigua*, *Palpifer sexno-* tata, *Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Siston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodesindicata, Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarchaderogata, Diaphania indica, Heliothis virescens* and *Earias cupreoviridis*; the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagons, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecaniumpersicae, Parlatoria theae, Pseudaonidia paeoniae, Empoasca onukii, Plautia stall, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatella, Eurydema pulchrum, Cletus trigonus, Clovia punctata, Empoasca* spp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopteruspruni, Aphis farinoseyanagicola, Metasalispopuli, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii*;

the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus,*

*Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans,* the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella;* the species of the order Hymenoptera such as *Pristomyrmex pungens,* the species of the family Bethylidae, *Monomorium pharaonis, Pheidole noda, Athalia rosae, Dryocosmus kuriphilus, Formica fusca japonica,* the species of the subfamily Vespinae, *Athalia infumata infumata, Arge pagana, Athalia japonica, Acromyrmex* spp., *Solenopsis* spp., *Arge mali* and *Ochetellus glaber;* the species of the order Orthoptera such as *Homorocoryphus lineosus, Gryllotalpasp., Oxya hyla intricata, Oxyayezoensis, Locusta migratoria, Oxya japonica, Homorocoryphus jezoensis* and *Teleogryllus emma;* the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei;* the species of the order Acari such as *Leptotrombidium akamushi, Tetranychus ludeni, Dermacentor variabilis, Tetranychus truncates, Ornithonyssus bacoti, Demodex canis, Tetranychus viennensis, Tetranychus kanzawai,* the species of the family Ixodidae such as *Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Brevipalpus* sp., *Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus;* the species of the order Blattodea such as *Periplaneta fuliginosa, Blattella germanica, Blatta orientalis, Periplaneta brunnea, Blattella lituricollis, Periplaneta japonica* and *Periplaneta americana;* the species of the order Siphonaptera such as *Pulex irritans, Ctenocephalides felis* and *Ceratophyllus gallinae;* the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans;* and the species of the phylum Mollusca such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, mites parasitic on animals are also included in the insect pests to be controlled, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanesis; Dermanyssus gallinae;* the species of the genus *Ornithonyssus* such as *Ornithonyssus sylviarum* and *Ornithonyssus bursa;* the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai;* the species of the family Cheyletidae such as *Cheyletiella yasguri, Cheyletiella parasitivorax* and *Cheyletiella blakei;* the species of the superfamily Sarcoptoidea such as *Psoroptes cuniculi, Chorioptes bovis, Otodectes cynotis, Sarcoptes scabiei* and *Notoedres cati;* and the species of the family Demodicidae such as *Demodex canis.*

Other insect pests to be controlled include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus.*

Other insect pests to be controlled include ectoparasites of animals, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites of animals include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium*, intestinal *Sarcocystis, Toxoplasma* and *Cryptosporidium*.

As is clear from the above, the compound of the present invention can exterminate not only agricultural and horticultural insect pests but also a wide range of sanitary pests.

The agricultural and horticultural insecticide comprising the condensed heterocyclic compound represented by the general formula (I) of the present invention or a salt thereof as an active ingredient has a remarkable control effect on the above-described insect pests which damage lowland crops, field crops, fruit trees, vegetables, other crops, ornamental flowering plants, etc., and exerts the desired effect when applied to nursery facilities for seedlings, paddy fields, fields, fruit trees, vegetables, other crops, ornamental flowering plants, etc. and their seeds, paddy water, foliage, cultivation media such as soil, or the like around the expected time of insect pest infestation, i.e., before the infestation or upon the confirmation of the infestation. Particularly preferred are embodiments utilizing so-called penetration and translocation of the agricultural and horticultural insecticide into crops, ornamental flowering plants, etc. In such embodiments, the compound of the present invention is applied to nursery soil, soil in transplanting holes, plant foot, irrigation water, cultivation water in hydroponics, or the like, and thereby absorbed through the plant roots via soil or otherwise.

The useful plants to which the agricultural and horticultural insecticide of the present invention can be applied include, but are not particularly limited to, for example, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins derived from *Bacillus cereus* or *Bacillus popilliae*; *Bacillus thuringiensis*-derived delta-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode-derived insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: delta-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining domains derived from these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control various insect pests, the agricultural and horticultural insecticide of the present invention, with or without appropriate dilution or suspension in water etc., is applied to plants potentially infested with insect pests and nematodes in an amount effective for control of the insect pests or the nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with insect pests in an amount effective for control of the insect pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing and dust coating of seeds with a liquid or solid formulation for the adherence of the formulation onto the surfaces of the seeds; coating of seeds with a mixture of a liquid or solid formulation and an adhesive carrier such as resins and polymers; and application of a liquid or solid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

In the method of the present invention for using an agricultural and horticultural insecticide, the term "soil" or "cultivation medium" refers to a support medium for crop cultivation, in particular a support medium which allows crop plants to spread roots therein, and the materials are not particularly limited as long as plants can grow. Examples of the support medium include so-called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application time, in other words, depending on the cultivation stage such as seeding time, greening period and planting time. A formulation such as a dust, a water-dispersible granule, a granule or the like may be mixed with soil. For example, such a formulation is incorporated into bed soil, covering soil or the whole soil. Simply, soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer or the like, may be applied onto soil or injected into soil. In addition, a solution of an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting. The agricultural and horticultural insecticide of the present invention is commonly used as a formulation convenient for application, which is prepared in the usual method for preparing agrochemical formulations.

That is, the condensed heterocyclic compound represented by the general formula (I) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. These additives may be used alone or in a combination of two or more kinds.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). These solid carriers may be used alone or in a combination of two or more kinds.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as gamma-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. These liquid carriers may be used alone or in a combination of two or more kinds.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. These surfactants may be used alone or in a combination of two or more kinds.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The content of the active ingredient compound in the agricultural and horticultural insecticide of the present invention can be adjusted as needed, and for example, is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the content of the active ingredient compound is 0.01 to 50 parts by weight (0.01 to 50% by weight relative to the total weight of the agricultural and horticultural insecticide).

The application amount of the agricultural and horticultural insecticide of the present invention may vary with various factors, for example, the purpose, the target insect pest, the growing conditions of crops, the tendency of insect pest infestation, the weather, the environmental conditions, the dosage form, the application method, the application site, the application time, etc., but for example, the application amount of the active ingredient compound per 10 ares is appropriately selected from the range of 0.001 g to 10 kg, and preferably 0.01 g to 1 kg depending on the purpose.

Furthermore, for the expansion of the range of target insect pests to be controlled and the appropriate application time for control of insect pests, or for dose reduction, the agricultural and horticultural insecticide of the present invention can be used after mixed with other agricultural or horticultural insecticides, miticides, nematicides, microbicides, biopesticides and/or the like. Further, the agricultural and horticultural insecticide can be used after mixed with herbicides, plant growth regulators, fertilizers and/or the like depending on its application.

Examples of such additional agricultural and horticultural insecticides, miticides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensis israelensis, Bacillus thuringiensis japonensis, Bacillus thuringiensis kurstaki* and *Bacillus thuringiensis tenebrionis*, BPMC, Bt toxin-derived insecticidal compounds, chlorfenson (CPCBS), dichlorodiisopropyl ether (DCIP), 1,3-dichloropropene (D-D), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, phenisobromolate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Examples of the agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, inorganic microbicides such as basic copper chloride, basic copper sulfate and silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Further, examples of the herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, a zafenidin, acifluorfen, a ziprotryne, a zimsulfuron, asulam, acetochlor, atrazine, atraton, anisuron, anilofos, aviglycine, abscisic acid, amicarba zone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarba zone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosuifuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuronmethyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Examples of the biopesticides include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor,* avirulent *Erwinia carotovora* and *Bacillus subtilis*; and biopesticides used as a herbicide, such as *Xanthomonas campestris*. A combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLES

Reference Example 1

Production of N-methyl-3-amino-6-trifluoromethyl pyridazine

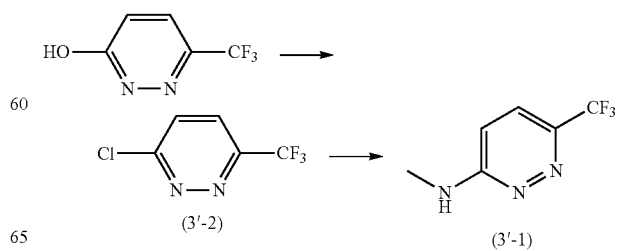

A mixture of 6-trifluoromethyl-3-pyridazinol (11.5 g) synthesized according to the method described in WO 2005/047279, thionyl chloride (12.5 g) and dimethylformamide (1 ml) was heated under reflux for 3 hours. Iced water was added to the reaction mixture, and extraction with ethyl acetate was performed. The organic layer was dried over anhydrous magnesium sulfate and then concentrated in vacuo. The residue was dissolved in tetrahydrofuran (5 ml), and to the solution, methylamine (40% methanol solution, 16.2 g) was added dropwise under ice cooling. The mixture was stirred at room temperature overnight, water was added to the reaction mixture, and extraction with ethyl acetate was performed. The organic layer was dried over anhydrous magnesium sulfate and then concentrated in vacuo. The resulting residue was subjected to column chromatography to give the desired compound (3'-1) (5.1 g).

Physical property: 150 to 152° C.

Reference Example 2

Synthesis of N-methyl-3-amino-4-bromo-6-trifluoromethyl pyridazine

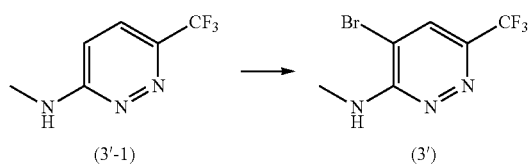

A mixture of N-methyl-3-amino-6-trifluoromethyl pyridazine (3'-1) (1.8 g) produced in Reference Example 1, 3,5-dibromohydantoin (3.15 g) and acetonitrile (10 ml) was heated under reflux for 3 hours. A saturated sodium hydrogen thiosulfate solution was added to the reaction mixture, and extraction with ethyl acetate was performed. The organic layer was dried over anhydrous magnesium sulfate and then concentrated in vacuo. The resulting residue was subjected to column chromatography to give the desired compound (3') (0.9 g).

Physical property: $^1$H-NMR (CDCl$_3$): 7.70 (s, 1H), 5.41 (brs, 1H), 3.26 (d, 1H)

Production Example 1-1

Production of 2-(2-fluoro-4-trifluoromethylphenyl)-3-methyl-6-trifluoromethyl-3H-imidazo[4,5-C]pyridazine

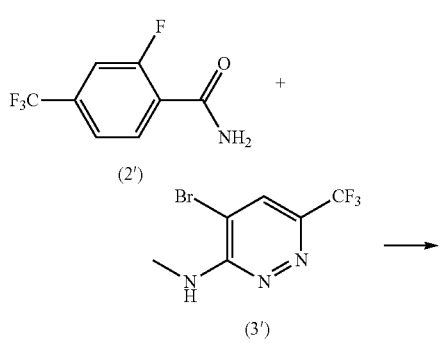

A mixture of N-methyl-3-amino-4-bromo-6-trifluoromethyl pyridazine (3') (475 mg) produced in Reference Example 2, 2-fluoro-4-trifluoromethyl benzoic acid amide (2') (500 mg), potassium t-butoxide (311 mg), [(diphenylphosphino) ferrocene]dichloro palladium (151 mg) and toluene (5 ml) was heated under reflux in argon atmosphere for 12 hours. Water was added to the reaction mixture, and extraction with ethyl acetate was performed. The organic layer was dried over anhydrous magnesium sulfate and then concentrated in vacuo. The resulting residue was subjected to column chromatography to give the desired compound (I'-2) (0.16 g).

Physical property: $^1$H-NMR (CDCl$_3$): 8.21 (s, 1H), 7.97 (t, 1H), 7.72 (d, 1H), 7.64 (d, 1H), 4.12 (d, 3H)

Production Example 1

Production of 2-(2-ethylthio-4-trifluoromethylphenyl)-3-methyl-6-trifluoromethyl-3H-imidazo[4,5-C]pyridazine (hereinafter, abbreviated to 1-1)

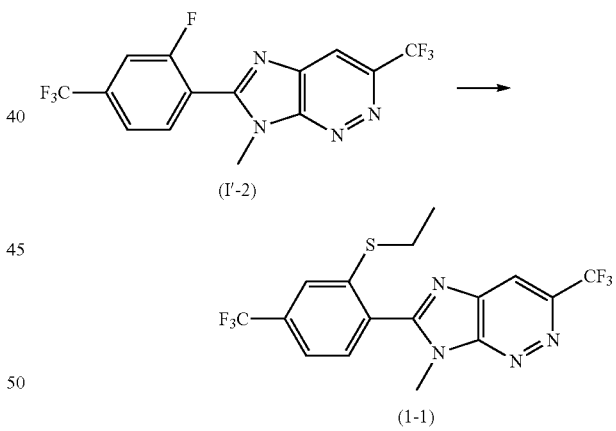

To a mixture of 2-(2-fluoro-4-trifluoromethylphenyl)-3-methyl-6-trifluoromethyl-3H-imidazo[4,5-C]pyridazine (I'-2) (160 mg) produced in Production Example 1-1 and DMF (2 ml), sodium ethanethiolate (60 mg) was added, and the mixture was stirred at 100° C. for 2 hours. After the reaction mixture was left to cool down, water was added to the reaction mixture, and extraction with ethyl acetate was performed. The organic layer was dried over anhydrous magnesium sulfate and then concentrated in vacuo. The resulting residue was subjected to column chromatography to give the desired compound (1-1) (183 mg).

Physical property: $^1$H-NMR (CDCl$_3$): 8.20 (s, 1H), 7.75 (s, 1H), 7.64 (d, 2H), 3.99 (s, 3H), 3.00 (dd, 2H), 1.26 (t, 3H)

Production Example 2

Production of 2-(2-ethylsulfonyl-4-trifluoromethyl-phenyl)-3-methyl-6-trifluoromethyl-3H-imidazo[4,5-C]pyridazine (1-3)

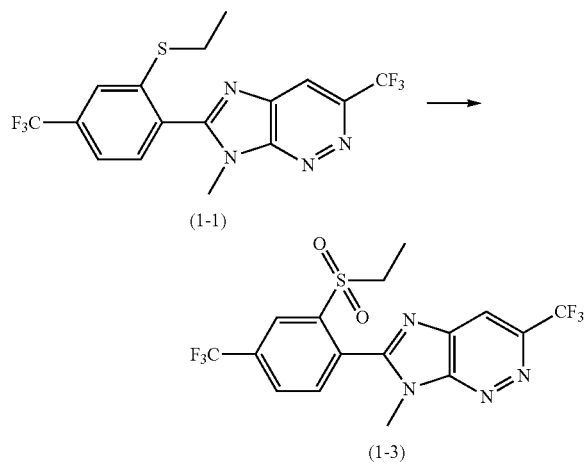

(1-1)

(1-3)

A mixture of 2-(2-ethylthio-4-trifluoromethylphenyl)-3-methyl-6-trifluoromethyl-3H-imidazo[4,5-C]pyridazine (1-1) (100 mg) produced in Production Example 1, ethyl acetate (3 ml) and m-chloroperoxybenzoic acid (85 mg) was stirred at room temperature for 3 hours. To the reaction mixture, 10 drops of formaldehyde dimethyl dithioacetal S-oxide were added, and the mixture was concentrated in vacuo. The resulting residue was subjected to column chromatography to give the desired compound (1-3) (87 mg).

Physical property: 161 to 163° C.

Hereinafter, formulation examples are shown, but the present invention is not limited thereto. In the formulation examples, the "parts" means parts by weight.

Formulation Example 1

| | |
|---|---|
| Compound (I) of the present invention | 10 parts |
| Xylene | 70 parts |
| N-methyl pyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate.

Formulation Example 2

| | |
|---|---|
| Compound (I) of the present invention | 3 parts |
| Clay powder | 82 parts |
| Diatomite powder | 15 parts |

The above ingredients are uniformly mixed and then pulverized to give a dust.

Formulation Example 3

| | |
|---|---|
| Compound (I) of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granule.

Formulation Example 4

| | |
|---|---|
| Compound (I) of the present invention | 20 parts |
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder.

Hereinafter, test examples in connection with the present invention are shown, but the present invention is not limited thereto.

Test Example 1

Test of Control Effect on *Myzus persicae*

Chinese cabbage plants were planted in plastic pots (diameter: 8 cm, height: 8 cm), green peach aphids (*Myzus persicae*) were propagated on the plants, and the number of surviving green peach aphids in each pot was counted. The condensed heterocyclic compounds represented by the general formula (I) of the present invention or salts thereof were separately dispersed in water and diluted to 500 ppm, and the agrochemical dispersions were applied to the foliage of the potted Chinese cabbage plants. After the plants were air-dried, the pots were kept in a greenhouse. At 6 days after the foliar application, the number of surviving green peach aphids on the Chinese cabbage plant in each pot was counted, the control rate was calculated according to the formula shown below, and the control effect was evaluated according to the criterion shown below.

Control rate=$100-\{(T \times Ca)/(Ta \times C)\} \times 100$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot Criterion
A: the control rate is 100%.
B: the control rate is 90 to 99%.
C: the control rate is 80 to 89%.
D: the control rate is 50 to 79%.

As a result, the compounds 1-1, 1-2, 1-3, 1-6, 1-10, 1-12, 1-13, 1-14, 1-15, 1-16, 1-18, 1-33, 1-34, 1-35, 1-36, 1-37, 1-39, 1-42, 1-61, 1-62, 1-63, 1-66, 2-10, 2-11, 2-12, 3-7, 3-52, 4-1, 4-2, 4-3, 4-4, 4-5, 4-6, 4-9, 4-12, 4-15, 4-18, 5-1, 5-7, 5-8, 5-9, 5-10, 5-11, 5-13, 6-1, 6-12, 6-13, 6-14 and 6-15 of the present invention showed the activity level evaluated as A.

Test Example 2

Test of Insecticidal Effect on *Laodelphax striatella*

The condensed heterocyclic compounds represented by the general formula (I) of the present invention or salts thereof were separately dispersed in water and diluted to 500 ppm, and rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatella*, and then the glass test tubes were capped with cotton plugs. At 8 days after the inoculation, the numbers of surviving larvae and dead larvae were counted, the corrected mortality rate was calculated according to the formula shown below, and the insecticidal effect was evaluated according to the criterion of Test Example 1.

Corrected mortality rate (%)=100×(Survival rate in a non-treatment plot−Survival rate in a treatment plot)/Survival rate in a non-treatment plot As a result, the compounds 1-1, 1-2, 1-3, 1-6, 1-10, 1-12, 1-13, 1-14, 1-15, 1-16, 1-18, 1-33, 1-34, 1-35, 1-36, 1-37, 1-39, 1-42, 1-61, 1-62, 1-63, 1-64, 1-66, 2-12, 4-1, 4-2, 4-3, 4-4, 4-5, 4-6, 4-9, 4-12, 4-15, 4-18, 5-1, 5-3, 5-7, 5-8, 5-9, 5-10, 5-13, 6-1, 6-12, 6-13, 6-14 and 6-15 of the present invention showed the activity level evaluated as A.

Test Example 3

Test of Insecticidal Effect on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different condensed heterocyclic compound represented by the general formula (I) of the present invention as an active ingredient. The seedlings were air-dried and then kept in a thermostatic chamber at 25° C. At 6 days after the dip treatment, the number of hatched larvae per plot was counted, the mortality rate was calculated according to the formula shown below, and the insecticidal effect was evaluated according to the criterion of Test Example 1. This test was conducted in triplicate using 10 adults of *Plutella xylostella* per plot.

Corrected mortality rate (%)=100×(Number of hatched larvae in a non-treatment plot−Number of hatched larvae in a treatment plot)/Number of hatched larvae in a non-treatment plot As a result, the compounds 1-1, 1-2, 1-3, 1-6, 1-10, 1-12, 1-13, 1-14, 1-15, 1-16, 1-18, 1-33, 1-34, 1-35, 1-36, 1-37, 1-39, 1-42, 1-61, 1-62, 1-63, 1-64, 1-66, 2-1, 2-2, 2-12, 3-1, 3-7, 4-1, 4-2, 4-3, 4-4, 4-5, 4-6, 4-9, 4-12, 4-15, 4-18, 5-1, 5-3, 5-7, 5-8, 5-9, 5-10, 5-13, 6-1, 6-12, 6-13, 6-14 and 6-15 of the present invention showed the activity level evaluated as A.

INDUSTRIAL APPLICABILITY

The compound of the present invention has an excellent control effect on a wide range of agricultural and horticultural insect pests and thus is useful.

The invention claimed is:
1. A condensed heterocyclic compound represented by formula (I):

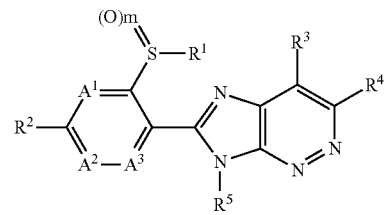

wherein:
$R^1$ is
(a1) a $(C_1-C_6)$ alkyl group;
(a2) a $(C_3-C_6)$ cycloalkyl group;
(a3) a $(C_2-C_6)$ alkenyl group;
(a4) a $(C_2-C_6)$ alkynyl group;
(a5) a halo $(C_1-C_6)$ alkyl group;
(a9) a $(C_1-C_6)$ alkoxy $(C_1-C_6)$ alkyl group;
(a11) a $(C_3-C_6)$ cycloalkyl $(C_1-C_6)$ alkyl group;
(a15) a $(C_1-C_6)$ alkylthio $(C_1-C_6)$ alkyl group;
(a16) a $(C_1-C_6)$ alkylsulfinyl $(C_1-C_6)$ alkyl group;
(a17) a $(C_1-C_6)$ alkylsulfonyl $(C_1-C_6)$ alkyl group;
(a18) a cyano $(C_1-C_6)$ alkyl group;
(a19) a $(C_1-C_6)$ alkoxycarbonyloxy $(C_1-C_6)$ alkyl group;
(a20) a di-$(C_1-C_6)$ alkylamino $(C_1-C_6)$ alkyl group (wherein the alkyl groups of the di-$(C_1-C_6)$ alkylamino moiety may be the same or different);
(a21) a phenyl $(C_1-C_6)$ alkyl group; or
(a22) a phenyl $(C_1-C_6)$ alkyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group,
$R^2$ is
(b1) a halogen atom;
(b4) a $(C_1-C_6)$ alkyl group;
(b5) a $(C_3-C_6)$ cycloalkyl group;
(b6) a $(C_2-C_6)$ alkenyl group;
(b7) a $(C_2-C_6)$ alkynyl group;
(b8) a halo $(C_1-C_6)$ alkyl group;
(b12) a $(C_1-C_6)$ alkylthio group;
(b15) a halo $(C_1-C_6)$ alkylthio group;
(b16) a halo $(C_1-C_6)$ alkylsulfinyl group;
(b17) a halo $(C_1-C_6)$ alkylsulfonyl group;
(b24) a hydrogen atom;
(b25) a $(C_1-C_6)$ alkoxy group;
(b26) a halo $(C_1-C_6)$ alkoxy group;
(b27) an amino group;
(b29) a di-$(C_1-C_6)$ alkylamino group (wherein the alkyl groups of the di-$(C_1-C_6)$ alkyl moiety may be the same or different);
(b30) a $(C_1-C_6)$ alkylcarbonylamino group;
(b31) a $(C_1-C_6)$ alkylsulfonylamino group;
(b32) a $(C_1-C_6)$ alkylsulfonyl $((C_1-C_6)$ alkyl) amino group;
(b33) a $(C_1-C_6)$ alkoxycarbonyl group; or
(b34) a tri-$(C_1-C_6)$ alkylsilyl $(C_2-C_6)$ alkynyl group (wherein the alkyl groups of the tri-$(C_1-C_6)$ alkylsilyl moiety may be the same or different),
$R^3$ is a hydrogen atom,
$R^4$ is
(d2) a halogen atom;
(d5) a $(C_1-C_6)$ alkyl group;

(d9) a halo $(C_1-C_6)$ alkyl group;
(d19) a mercapto group;
(d20) a $(C_1-C_6)$ alkylthio group;
(d21) a $(C_1-C_6)$ alkylcarbonylthio group;
(d22) a halo $(C_1-C_6)$ alkylthio group;
(d24) a phenyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group; or
(d26) a $(C_1-C_6)$ alkylsulfonyl group,
  $R^5$ is
(e3) a $(C_1-C_6)$ alkyl group;
(e4) a $(C_3-C_6)$ cycloalkyl group;
(e5) a halo $(C_1-C_6)$ alkyl group;
(e9) a $(C_1-C_6)$ alkoxy $(C_1-C_6)$ alkyl group;
(e13) an amino group; or
(e14) a $(C_1-C_6)$ alkoxy group,
  each of $A^1$ and $A^2$ represents a C—$R^6$ group (wherein $R^6$ is a hydrogen atom),
  $A^3$ represents a nitrogen atom or a C—$R^6$ group (wherein $R^6$ is a hydrogen atom), and
  m represents 0, 1 or 2, or
a salt thereof.

2. The condensed heterocyclic compound according to claim 1,
wherein:
  $R^1$ is
(a1) a $(C_1-C_6)$ alkyl group;
(a2) a $(C_3-C_6)$ cycloalkyl group;
(a3) a $(C_2-C_6)$ alkenyl group;
(a5) a halo $(C_1-C_6)$ alkyl group;
(a11) a $(C_3-C_6)$ cycloalkyl $(C_1-C_6)$ alkyl group;
(a15) a $(C_1-C_6)$ alkylthio $(C_1-C_6)$ alkyl group;
(a18) a cyano $(C_1-C_6)$ alkyl group;
(a19) a $(C_1-C_6)$ alkoxycarbonyloxy $(C_1-C_6)$ alkyl group;
(a20) a di-$(C_1-C_6)$ alkylamino $(C_1-C_6)$ alkyl group (wherein the alkyl groups of the di-$(C_1-C_6)$ alkylamino moiety may be the same or different); or
(a22) a phenyl $(C_1-C_6)$ alkyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group,
  $R^2$ is
(b1) a halogen atom;
(b4) a $(C_1-C_6)$ alkyl group;
(b5) a $(C_3-C_6)$ cycloalkyl group;
(b6) a $(C_2-C_6)$ alkenyl group;
(b7) a $(C_2-C_6)$ alkynyl group;
(b8) a halo $(C_1-C_6)$ alkyl group;
(b12) a $(C_1-C_6)$ alkylthio group;
(b15) a halo $(C_1-C_6)$ alkylthio group;
(b24) a hydrogen atom;
(b26) a halo $(C_1-C_6)$ alkoxy group;
(b27) an amino group;
(b29) a di-$(C_1-C_6)$ alkylamino group (wherein the alkyl groups of the di-$(C_1-C_6)$ alkyl moiety may be the same or different);
(b30) a $(C_1-C_6)$ alkylcarbonylamino group;
(b31) a $(C_1-C_6)$ alkylsulfonylamino group;
(b32) a $(C_1-C_6)$ alkylsulfonyl $((C_1-C_6)$ alkyl)amino group;
(b33) a $(C_1-C_6)$ alkoxycarbonyl group; or
(b34) a tri-$(C_1-C_6)$ alkylsilyl $(C_2-C_6)$ alkynyl group (wherein the alkyl groups of the tri-$(C_1-C_6)$ alkylsilyl moiety may be the same or different),
  $R^3$ is a hydrogen atom,
  $R^4$ is
(d2) a halogen atom;
(d9) a halo $(C_1-C_6)$ alkyl group;
(d19) a mercapto group;
(d20) a $(C_1-C_6)$ alkylthio group;
(d21) a $(C_1-C_6)$ alkylcarbonylthio group;
(d22) a halo $(C_1-C_6)$ alkylthio group;
(d24) a phenyl group having, on the ring, 1 to 5 substituting groups selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group; or
(d26) a $(C_1-C_6)$ alkylsulfonyl group,
  $R^5$ is
(e3) a $(C_1-C_6)$ alkyl group;
(e4) a $(C_3-C_6)$ cycloalkyl group; or
(e9) a $(C_1-C_6)$ alkoxy $(C_1-C_6)$ alkyl group,
or
a salt thereof.

3. An ectoparasite control composition comprising a condensed heterocyclic compound or a salt thereof according to claim 1 as an active ingredient and an additive.

4. An insecticide composition comprising a condensed heterocyclic compound or a salt thereof according to claim 1 as an active ingredient and an additive.

5. An ectoparasite control composition comprising a condensed heterocyclic compound or a salt thereof according to claim 2 as an active ingredient and an additive.

6. A method for controlling an agricultural and horticultural insect pest, comprising treating a plant or soil with an effective amount of an agricultural and horticultural insecticide comprising a condensed heterocyclic compound or a salt thereof according to claim 1 as an active ingredient.

7. A method for controlling an ectoparasite, comprising treating the ectoparasite with an effective amount of the ectoparasite control composition according to claim 3.

8. A method for controlling an agricultural and horticultural insect pest, comprising treating a plant or soil with an effective amount of an agricultural and horticultural insecticide comprising a condensed heterocyclic compound or a salt thereof according to claim 2 as an active ingredient.

9. A method for controlling an ectoparasite, comprising treating the ectoparasite with an effective amount of the ectoparasite control composition according to claim 5.

* * * * *